United States Patent [19]

Schwartz et al.

[11] Patent Number: 5,028,631

[45] Date of Patent: Jul. 2, 1991

[54] HOMOANDROSTAN-17-ONE AND HOMOANDROSTEN-17-ONES

[76] Inventors: Arthur G. Schwartz, 220 Locust St., Philadelphia, Pa. 19106; Marvin L. Lewbart, 546 E. Saint Andrews Dr., Media, Pa. 19063

[21] Appl. No.: 126,912

[22] Filed: Nov. 25, 1987

[51] Int. Cl.$^5$ .................. C07C 49/23; C07C 49/297
[52] U.S. Cl. .................. 514/691; 568/369; 568/372; 568/612; 568/817; 570/187
[58] Field of Search ............... 568/372, 369, 612, 817; 570/187; 585/21; 514/691

[56] References Cited

U.S. PATENT DOCUMENTS

| | | | |
|---|---|---|---|
| 2,833,793 | 5/1958 | Dodson et al. | |
| 2,847,457 | 8/1958 | Johnson et al. | 568/372 |
| 2,911,418 | 11/1959 | Johns et al. | |
| 3,076,023 | 1/1963 | Kaspar et al. | 568/369 |
| 3,148,198 | 9/1964 | Goldkamp et al. | |
| 3,150,184 | 9/1964 | Moersch et al. | 568/369 |
| 3,194,831 | 7/1965 | Reimann et al. | 568/372 |
| 3,206,472 | 9/1965 | Nagata | 568/372 |
| 3,264,345 | 8/1966 | Moersch et al. | 568/372 |
| 3,403,167 | 9/1968 | Nagata | 568/372 |
| 3,471,480 | 10/1969 | Fritsch et al. | |
| 3,642,800 | 2/1972 | Nelson et al. | 568/372 |
| 3,976,691 | 8/1976 | Middleton et al. | |
| 4,628,052 | 12/1986 | Peat et al. | |

FOREIGN PATENT DOCUMENTS

| | | |
|---|---|---|
| 133995 | 3/1985 | European Pat. Off. |
| 210665 | 2/1987 | European Pat. Off. |
| 55220 | 8/1943 | Fed. Rep. of Germany ...... 568/372 |
| 1239306 | 4/1964 | Fed. Rep. of Germany |
| 2035738 | 6/1970 | Fed. Rep. of Germany |
| 2705917 | 2/1977 | Fed. Rep. of Germany |
| 2317934 | 2/1977 | France |
| 989503 | 8/1963 | United Kingdom |

OTHER PUBLICATIONS

"D-Homo-steroids. Part I. Derivatives Monosubstituted in Ring D", Kirk et al., J. Chem. Soc. (C), 1970, pp. 1454–1460.
"A Theory for the Quantitative Calculation of the Amplitudes of Cotton Effect Curves of Ketones", Tai et al., J. Am. Chem. Soc. 88:2179 & 2185 (1965).
"Conformational Analysis. XXXVIII. The Conformations of Cxyclohexanone Rings", Chem. Abst. 61:13365h (1964).
"4–Epifriedelin and 4–Epishionone. Structure and Reflex Effect", Aoyagi et al., Chem. Abst. 78:148091 (1973).

(List continued on next page.)

Primary Examiner—H. M. S. Sneed
Assistant Examiner—J. Saba
Attorney, Agent, or Firm—Scully, Scott, Murphy & Presser

[57] ABSTRACT

Compounds of the formula:

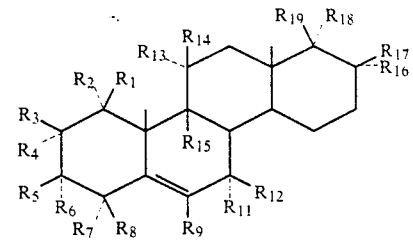

and

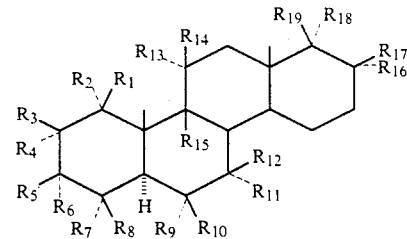

useful as anti-cancer agents, anti-obesity agents, anti-hyperglycemic agents, anti-aging agents, anti-hyperglycemic agents and anti-autoimmune agents.

91 Claims, 4 Drawing Sheets

OTHER PUBLICATIONS

"Acid Catalyzed Dehydration and Rearrangement of 17-Beta; 17-Alpha, Beta-Diols in the 17a-alphamethyl-D-homoandrostane Series", Monneret et al., Chem. Abst. 73:45668 (1970).

"Backbone Rearrangements of Andros-5-ene and D-Homoandrost-5-ene Novel Recemization", Kirk et al., Chem. Abst. 75:118444 (1971).

D-Homoandrostane Chem. Abst. Index Guide 1987.

Hanson et al., *Perkin Transactions I*, (1977), pp. 499–501.

Numazawa et al., *Steroids*, 32, 519–527 (1978).

Abou-Gharbia et al., *Journal of Pharmaceutical Sciences*, 70, 1154–1157 (1981).

Pashko et al., *Carcinogenesis*, 2, 717–721 (1981).

Pashko et al., *Carcinogenesis*, 5, 463–466 (1984).

Raineri and Levy, *Biochemistry*, 9, 2233–2243 (1970).

Robinson et al., *J. Org. Chem*, 28, 975–980 (1963).

Neef et al., *J. of Org. Chem.*, 43, 4679–4680 (1978).

Gordon et al., *Cancer Research 46, 3389–3395 (1986)*.

Julian et al, in *JACS*, 70, 3872–3876 (1948).

Ross et al. in *J. Chem. Soc.*, 25–27 (1945).

Pelc et al. in *Collection Czechoslov. Chem. Commun.* 31, 1064–1071 (1966).

Klimstra et al. in *Journal of Med. Chem.*, 9, 924–929 (1966).

Bridgeman et al. in *J. Chem. Soc.* C, 250–257 (1970).

Mailloux et al. in *Bulletin de la Societe Chimique de France*, 617–621 (1969).

Chemical Abstracts, 67, 54331k (1967).

Catsoulacos et al. in *J. Org. Chem.*, 32, 3723–3724 (1967).

Sheppard et al. in *Some Chemistry of 13-Iso-Steroids*, 2551–2558 (1977).

Crabb et al. in *J.C.S. Perkin I*, 1041–1045 (1981).

Chemical Abstracts 92, 215616v (1980).

Bird et al, in *J.C.S. Perkin I*, 750–755 (1980).

Kirk et al., in *J.C.S. Perkin I*, 762–779 (1976).

Chemical Abstracts 79, 42723 (1973).

Denny et al, in *J.C.S. Perkin I*, 486–492 (1972).

HOMOANDROSTAN-17-ONE AND HOMOANDROSTEN-17-ONES

BACKGROUND OF THE INVENTION

This invention relates to novel steroids and more particularly to androsterone derivatives useful as anti-cancer, anti-obesity, anti-diabetic and hypolipidemic agents.

Dehydroepiandrosterone (DHEA) and DHEA-sulfate are major adrenal secretory products in humans. The plasma concentration of DHEA-sulfate, which next to cholesterol, is the most abundant steroid in humans, undergoes the most marked age-related decline of any known steroid.

Although DHEA-sulfate is the main precursor of placental estrogen and may be converted into active androgens in peripheral tissue, there is no obvious biological role for either DHEA or DHEA-sulfate in the normal individual. Several retrospective and prospective studies suggest that women with sub-normal levels of these steroids may be predisposed to develop breast cancer. For example, see Brownsey, et al., "Plasma dehydroepiandrosterone sulfate levels in patients with benign and malignant breast disease," Eur. J. Cancer, 8, 131-137 (1972); Bulbrook, et al., "Relation between urinary androgen and corticoid excretion and subsequent breast cancer," Lancet, 2, 395-398 (1971); Rose, et al., "Plasma dehydroepiandrosterone sulfate, androstenedione and cortisol, and urinary free cortisol excretion in breast cancer, "Eur. J. Cancer, 13, 43-47 (1977); Wang, et al., "Studies of the sulfate esters of dehydroepiandorsterone and androsterone in the blood of women with breast cancer," Eur. J. Cancer, 10, 477-482 (1974); and Zumoff, et al., "Abnormal 24-hr mean Plasma concentrations of dehydroisoandrosterone and dehydroisoandrosterone sulfate in women with primary operable breast cancer," Cancer Research, 41, 3360-3363, September, 1981.

It has also been established that DHEA is a potent non-competitive inhibitor of mammalian glucose-6-phosphate dehydrogenase (G6PDH). For example, see Oertel, et al., "The effects of steroids on glucose-6-phosphate dehydrogenase," J. Steroid Biochem., 3, 493-496 (1972) and Marks, et al., "Inhibition of mammalian glucose-6-phosphate dehydrogenase by steroids," Proc. Nat'l Acad. Sci, USA, 46, 477-452 (1960). Moreover, Yen, et al., "Prevention of obesity in $A^{vy}/a$ mice by dehydroepiandrosterone," Lipids, 12, 409-413 (1977), reported that long-term administration of DHEA to VY-$A^{vy}/a$ mice prevented the development of obesity without suppressing appetite.

Furthermore, it is also known that the long-term treatment of C3H mice with DHEA, in addition to reducing weight gain without suppressing appetite, markedly inhibits spontaneous breast cancer development and may delay the rate of aging. It has been observed that DHEA antagonizes the capacity of the tumor promoter, 12-0-tetradecanoylphorbol-13-acetate, to stimulate $^3$H-thymidine incorporation in mouse epidermis and in a cultured rat kidney epithelial cell line. See, Schwartz, "Inhibition of spontaneous breast cancer formation in female C3H-$A^{vy}/a$ mice by long-term treatment with dehydroepiandrosterone, Cancer Res., 39, 1129-1132 (1979); and Schwartz, et al., "Dehydroepiandrosterone: an anti-obesity and anti-carcinogenic agent," Nut. Cancer 3, 46-53 (1981).

Ben-David, et al., "Anti-hypercholesterolemic effect of dehydroepiandrosterone in rats," Proc. Soc. Expt. Biol. Med., 125, 1136-1140 (1967) have observed that DHEA treatment has an anti-hypercholesterolemic effect in mice, while Coleman, et al. (Diabetes 31, 830, 1982) report that administration of DHEA produces a marked hypoglycemic effect in C57BL/KsJ-db/db mice. The latter authors suggest that the therapeutic effect of DHEA might result from its metabolism to estrogens.

It is further known that DHEA and 16α-bromoepiandrosterone are inhibitors of Epstein-Barr virus-induced transformation of human lymphocytes and that 16α-bromoepiandrosterone is a more potent inhibitor of mammalian G6PDH than DHEA. See, Schwartz, et al. Carcinogensis, Vol. 2 No. 7, 683-686 (1981).

While DHEA has been found effective in the afore-described manners, there is however, evidence of an estrogenic effect after prolonged administration. DHEA is not an estrogen per se but is well known to be convertible into estrogens. In addition, the therapeutic dose of DHEA is rather high. It would therefore be highly desirable to provide steroids, which while having the same afore-described advantage of DHEA are more potent and do not produce an estrogenic effect.

Besides DHEA, other steroids are known in the art.

Great Britain Patent No. 989,503 to Burn, et al. discloses 6,16β-dimethyl-3βhydroxyandrost-5-en-17-ones. These compounds are disclosed to be useful as possessing pituitary inhibiting action.

U.S. Pat. No. 2,833,793 to Dodson, et al. discloses 1β,3β-dihydroxy-5-androsten-17-one as an androgenic and anabolic agent.

U.S. Pat. No. 2,911,418 to Johns, et al. discloses 16α-chloro-3β-hydroxyandrost-5-en-17-one and 3β-hydroxy-16α-iodoandrost-5-en-17-one as an anti-androgen.

Goldkamp, et al. in U.S. Pat. No. 3,148,198 disclose that 16α,16β-difluoro-3β-hydroxyandrost-5-en-17-one possess androgenic properties.

French Application No. FR-A 2,317,934 discloses the following compounds:

3β-hydroxy-16{-methylandrost-5-en-17-one
3β-hydroxy-16{-ethylandrost-5-en-17-one
3β-hydroxy-16{-isopropylandrost-5-en-17-one U.S. Pat. No. 3,976,691 discloses the following compounds:

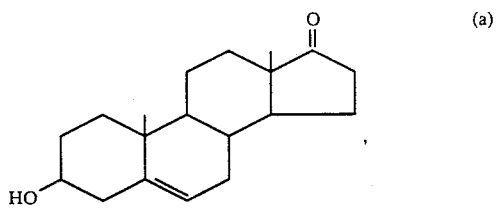

(a)

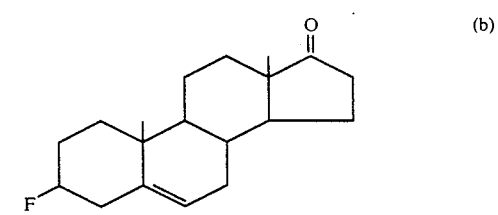

(b)

U.S. Pat. No. 3,471,480 to Fritsch, et al. discloses the following compounds which are useful as progestational agents:

(a) 3β-iodo-Δ⁵-6-methyl-17-oxoandrostene
(b) 3β-chloro-Δ⁵-6-methyl-17-oxoandrostene
(c) 3β-hydroxy-Δ⁵-6-methyl-17-oxoandrostene Hanson, et al. in Perkin Transactions I, 1977, pp. 499–501, disclose 3β,4β-dihydroxyandrost-5-en-17-one. No utility is disclosed.

Chemical Abstract 89:105866b discloses that 3β-hydroxy-5β-androstan-17-one can be hydroxylated in the 15β-position. Furthermore, said reference teaches that hydroxylation of 3β-hydroxy-5αandrosten-17-one gave both the 7α and 7β-hydroxyisoandrosterones.

Numazawa, et al. in *Steroids*, 32, 519–527 disclose 3β,16α-dihydroxyandrost-5-en-17-one. No utility is disclosed.

DE-A- 2,035,738 discloses 7α-Methyl-3β-hydroxy-5-androsten-17-one and 6,7α-dimethyl-3β-hydroxy-5-androsten-17-one.

DE-A2 705917 discloses 3β,16β-dihydroxy-5-androsten-17-one.

The Annual Report of the Fels Research Institute, pp. 32–33, (1979–1980) discloses the following compounds as having tumor-preventive, anti-obesity and anti-aging qualities:

3β-hydroxy-16α-bromo-5α-androstan-17-one
3β-hydroxy-16α-chloro-5α-androstan-17-one
3β-hydroxy-16α-fluoro-5α-androstan-17-one
3β-hydroxy-16α-iodo-5α-androstan-17-one
3β-hydroxy-16α-bromoandrost-5-ene-17-one
16βbromoandrostan-17-one Abou-Gharbia, et al. in *Journal of Pharmaceutical Sciences*, 70, 1154–1156 (1981) disclose the syntheses of:
3β-hydroxy-16α-chloro-5α-androstan-17-one,
3β-hydroxy-16α-fluoro-5α-androstan-17-one,
3β-hydroxy-16α-bromo-5α-androstan-17-one ,
3β-hydroxy-16α-iodo-5α-androstan-17-one.

Pashko, et al. in *Carcinogenesis*, 2, 717–721 (1981) disclose that 16α-Br-epiandrosterone is more active than DHEA in inhibiting G6PDH and in reducing the rate of [³H] thymidine incorporation into mouse breast epithilum and epidermis. The authors suggest that this compound may be useful in suppressing breast cancer development.

Neef, et al. in *Journal of Org. Chem.*, 43, 4679–4680 disclose the syntheses of 3β-hydroxy-16α-methyl-5-androsten-17-one and 3β-hydroxy-16β-methyl-5-androsten-17-one. androsten-17-one.

Robinson, et al. in *Journal of Org. Chem.*, 28, 975–980 (1963) disclose the synthesis of 3β-hydroxy-16α,16β-difluoro-5-androsten-17-one.

Rarnier, et al. in *Biochemistry*, 9, 2233–2243 (1970) tested the inhibitory activity of the following steroids on NADP and NAD linked activity of glucose 6-phosphate dehydrogenase:

3β-hydroxy-5α-androstan-17-one
3β-hydroxy-5β-androstan-17-one
3α-hydroxy-5α-androstan-17-one
11β-hydroxy-5α-androstan-17-one
3α-hydroxy-4α-methyl-5αandrostan-17-one
3α-hydroxy-7α-methyl-5αandrostan-17-one
3β-hydroxy-7α-methyl-5βandrostan-17-one
3β-hydroxy-16α-bromo-5αandrostan-17-one
3β-chloro-5α-androstan-17-one.

Gordon, et al. in Cancer Research 46, 3389–3395 (1986) disclose that DHEA, 16α-bromoepiandrosterone. epiandrosterone, 3β-hydroxy-5α-pregnan-20-one, 5α-androstan-17-one and 5α-androstan-3β,16α-diol-17-one are inhibitors of glucose 6-phosphate dehydrogenase. Furthermore, said reference discloses that testosterone, 17β-Estradiol, 5-androstene-3β,17βdiol, dehydroepiandrosterone-3-sulfate and 5α-androstan-17β-ol are noninhibitors of glucose-6-phosphate dehydrogenase. The reference suggests that there is a general correlation between the structure requirements for blocking differentiation to adipocytes and inhibiting glucose-6-phosphate dehydrogenase.

Julian, et al. in *JACS*, 70, 3872–3876 (1948) discloses the preparation of 16-dimethylaminomethyldehydroisoandrosterone.

Peat in U.S. Pat. No. 4,628,052 discloses compositions containing the following compounds as the active ingredient:

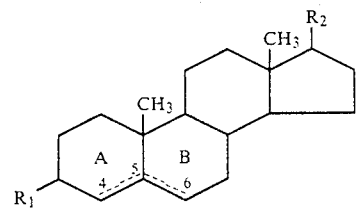

wherein R₁ is O or OH and R₂ is O, or OH; and which may contain one double bond in ring A and/or B or tocopherol.

The compounds are alleged to be useful in treating rheumatoid arthritis, osteoarthritis and arthritis associated with psoriasis and with lupus and other autoimmune diseases and also for treating non-specific joint pain associated with stress.

SUMMARY OF THE INVENTION

The present invention relates to novel steroids which are useful as cancer-preventive agents, anti-obesity agents, anti-hyperglycemic agents, anti-aging agents, anti-hypercholesterolemic agents and anti-autoimmune agents.

Moreover, the present invention is directed to novel steroids, useful as anti-cancer, anti-obesity, anti-hyperglycemic, anti-aging and anti-hypercholesterolemic agents, which do not evidence estrogenic effects.

Finally, the present invention is directed to the process for the treatment and/or prevention of cancer, obesity, aging, diabetes and hyperlipidemia.

Therefore, the present invention provides novel steroids of the general formula:

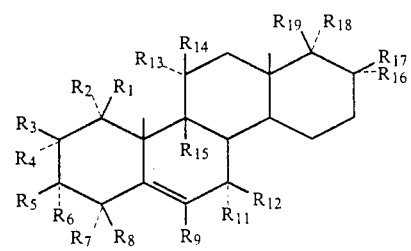

wherein
$R_1$, $R_2$, $R_3$, $R_4$, $R_5$, $R_6$, $R_7$, $R_8$, $R_{11}$, $R_{12}$, $R_{13}$, $R_{14}$, $R_{15}$ are each independently hydrogen, lower alkyl, halogen, hydroxy or lower alkoxy;

$R_9$ is hydrogen, lower alkyl or halogen; and $R_{16}$, $R_{17}$, $R_{18}$, or $R_{19}$ are each independently hydrogen, lower alkyl, hydroxy or halogen; or $R_{16}$ and $R_{17}$ taken together or $R_{18}$ and $R_{19}$ taken together are each independently oxo, with the proviso that said compound contains only one oxo group.

Further objectives are accomplished herein by providing novel steroids of the formula:

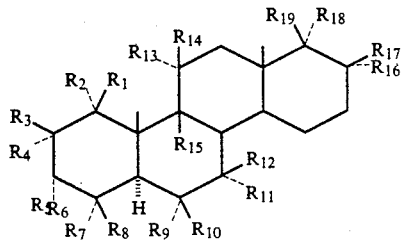

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are each independently hydrogen, lower alkyl, loweralkoxy, halogen or hydroxy; and $R_{16}$, $R_{17}$, $R_{18}$ or $R_{19}$ are each independently hydrogen, loweralkyl, hydroxy or halgoen; or $R_{16}$ and $R_{17}$ taken together or $R_{18}$ and $R_{19}$ taken together are each independently oxo, with the proviso that said compound contains only one oxo group.

The present invention is also directed to processes for the prophylaxis of cancer, obesity, aging, diabetes and hyperlipidemia and autoimmune diseases, such as lupus erythematosus or Coomb's positive hemolytic anemia, by administering to a host, e.g., mammals, a therapeutically effective amount of the afore-identified steroids.

DETAILED DESCRIPTION OF THE INVENTION

In accordance with the present invention, it has been surprisingly discovered that steroids having a certain structure, described hereinafter in more detail, are characterized with significant pharmacological properties without toxic or undesirable estrogenic effects. That is, it has been quite unexpectedly discovered that the steroids of the present invention are useful as cancer preventive, anti-obesity, anti-diabetic, anti-aging and anti-hypercholesterolemic agents, but unlike DHEA are more potent and exhibit very little or no estrogenic effects.

More particularly, the steroids of the present invention have the general formulae:

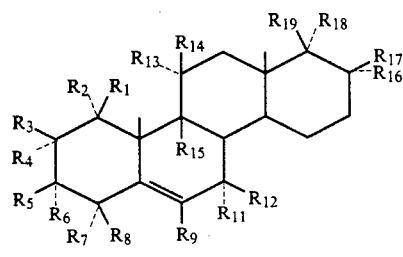

and

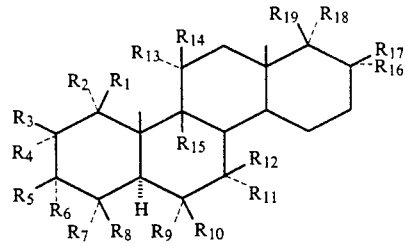

wherein $R_1$–$R_{19}$ are as defined hereinbefore. The $R_1$–$R_{19}$ substituents are designated as being in the α-position by means of a broken line(---) joining the substituent to the steroid nucleus, and the substituents are designated as being in the β-position by means of a solid line (—) joining the substituent to the steroid nucleus. In those cases in which the substituent may be either in the α- or β-position the substituents are indicated as being joined to the steroid nucleus by a wavy line. Furthermore, in accordance with I.U.P.A.C. nomenclature, the carbon atoms of the steroids of the present invention are numbered as follows and the steroids have the designated I.U.P.A.C. stereochemistry:

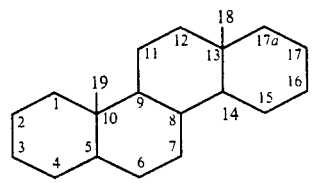

The present invention Provides processes for the prophylaxis of cancer, obestiy, aging, diabetes, and hyperlipidemia and autoimmune diseases, such as lupus erythematosus or Coomb's positive hemolytic anemia comprising administering to a host, e.g., mammals, a therapeutically effective amount of the present new steroids.

In accordance with the present invention, it has been surprisingly discovered that steroids having a certain structure, described hereinabove and hereinafter in more detail, are characterized with significant pharmacological properties without toxic or undesirable estrogenic effects. That is, it has been quite unexpectedly discovered that the steroids of the present invention are useful as cancer preventive, anti-obesity, anti-diabetic, anti-aging, anti-autoimmune and anti-hypercholesterolemic agents, but unlike DHEA are more potent and exhibit very little or no estrogenic effect. Furthermore, unlike DHEA, compounds of the present invention do not induce liver enlargement and increased catalase activity.

In the present invention, the alkyl groups are preferably lower alkyl, which may be straight or branched chain, and which contain up to 6 carbon atoms. Examples include methyl, ethyl, propyl, isopropyl, butyl, isobutyl, pentyl, amyl and the like. A preferred alkyl group contains 1-3 carbons. The most preferred alkyl group is methyl.

The halo atoms are preferably Br, F or Cl, especially F.

Additional variations in the structural formula representing the instant compounds can be effected without significantly altering the therapeutic properties. For example, the alkyl moieties can be substituted by one or more of a variety of substituents, such as hydroxy, halogen, alkyl and the like.

Preferred compounds of Formula I have the following formula:

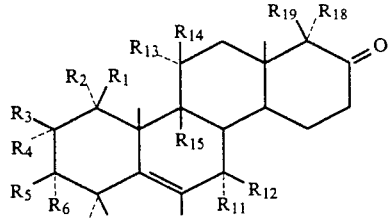

III and

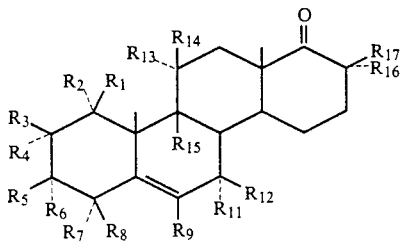

IV wherein $R_1$, $R_2$, $R_3$, $R_4$, $R_5$, $R_6$, $R_7$, $R_8$, $R_{11}$, $R_{12}$, $R_{13}$, $R_{14}$, and $R_{15}$ are each independently hydrogen, loweralkyl, halogen, hydroxy or loweralkoxy, $R_9$ is hydrogen, lower alkyl or halogen; and $R_{16}$, $R_{17}$, $R_{18}$ are each independently hydrogen, lower alkyl, hydroxy or halogen.

In the most preferred embodiment, $R_5$ is hydrogen or methyl. Furthermore, it is preferred that $R_1$, $R_2$, $R_3$, $R_4$, $R_6$, $R_7$, $R_8$, $R_9$, $R_{11}$, $R_{12}$, $R_{13}$, $R_{14}$ and $R_{15}$ are all hydrogen or at most one of $R_1$, $R_2$, $R_3$, $R_4$, $R_6$, $R_7$, $R_8$, $R_9$, $R_{11}$, $R_{12}$, $R_{13}$, $R_{14}$ and $R_{15}$ is other than hydrogen. Accordingly, the most preferred compounds of Formula I have the formulae:

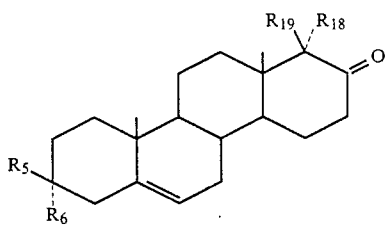

V and

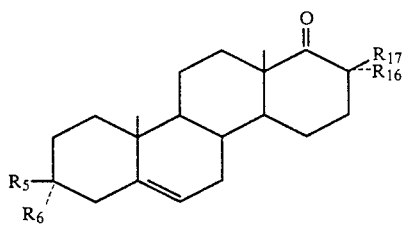

VI wherein $R_5$ and $R_6$ are independently loweralkyl or hydrogen; $R_{16}$, $R_{17}$, $R_{18}$ and $R_{19}$ are each independently hydrogen, lower alkyl or halogen.

Preferred compounds of Formula II have the following formula:

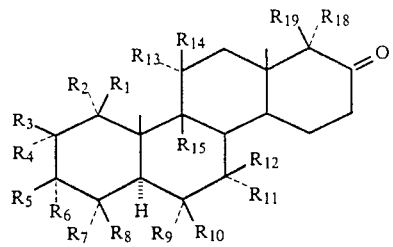

VII and

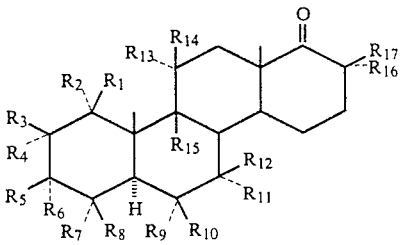

VIII wherein $R_1$, $R_2$ $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are each independently hydrogen, lower alkyl, loweralkoxy, halogen or hydroxy; and $R_{16}$, $R_{17}$, $R_{18}$ or $R_{19}$ are each independently hydrogen, loweralkyl, hydroxy or halgoen; or $R_{16}$ and $R_{17}$ taken together or $R_{18}$ and $R_{19}$ taken together are each independently oxo, with the proviso that said compound contains only one oxo group.

In the most preferred embodiment, $R_5$ is hydrogen or methyl. Furthermore, it is preferred that $R_1$, $R_2$, $R_3$, $R_4$, $R_6$, $R_7$, $R_8$, $R_9$, $R_{10}$, $R_{11}$, $R_{12}$, $R_{13}$, $R_{14}$ and $R_{15}$ are hydrogen or at most one of $R_1$, $R_2$, $R_3$, $R_4$, $R_6$, $R_7$, $R_8$, $R_9$, $R_{10}$, $R_{11}$, $R_{12}$, $R_{13}$, $R_{14}$ and $R_{15}$ is other than hydrogen. Accordingly, the most preferred compounds of Formula II have the formulae:

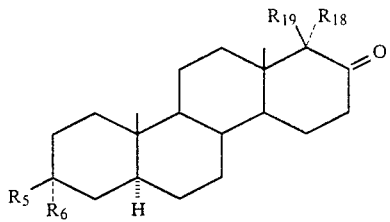

IX and

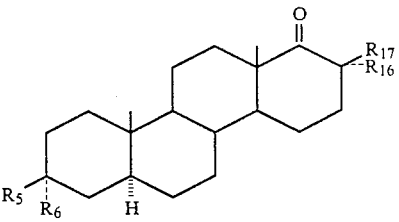

X wherein:

$R_5$ and $R_6$ are independently lower alkyl or hydrogen; and $R_{16}$, $R_{17}$, $R_{18}$ and $R_{19}$ are independently hydrogen, loweralkyl or halogen.

The steroids of the present invention may be prepared in accordance with conventional organic syntheses from known compounds or readily preparable intermediates. An exemplary general procedure for the synthesis of a useful intermediate, which, by the way, is encompassed by the present invention is as follows:

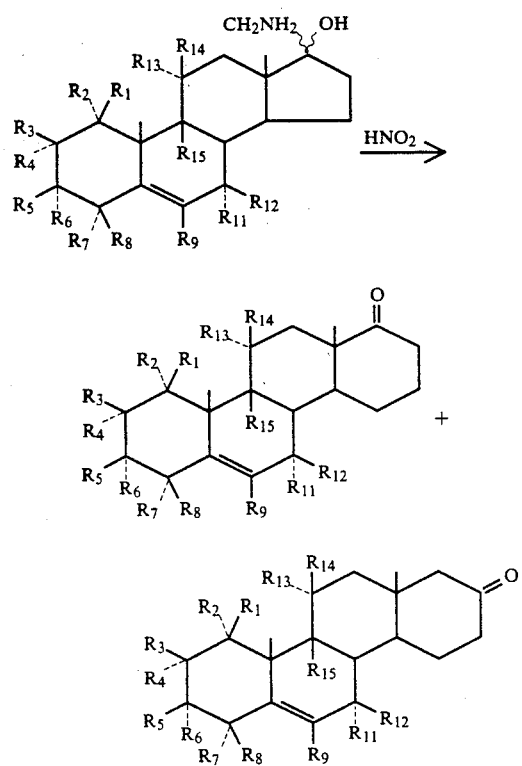

wherein $R_1$-$R_{15}$ each independently hydrogen or loweralkyl. Treatment of the 17{-hydroxy-17{aminomethyl (XI) with nitrous acid in acid, such as acetic acid and the like affords the homoandrostenones of Formula IIIA and IVA. XI, in turn is prepared by the reduction by hydride, such as LiAlH$_4$ of the corresponding C-17 cyanohydrins.

Similarly, the 5α-homoandrostan 17- and 17a-ones can be prepared as follows:

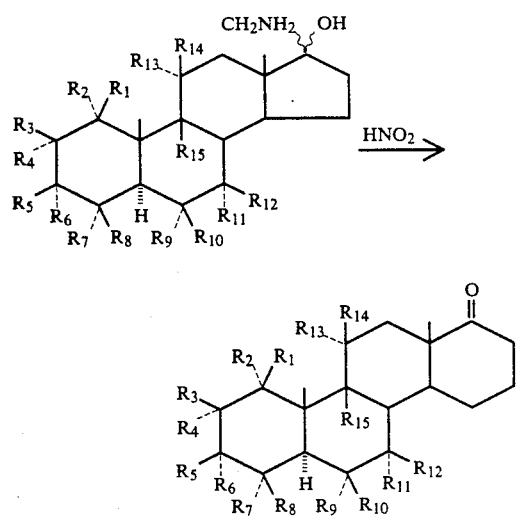

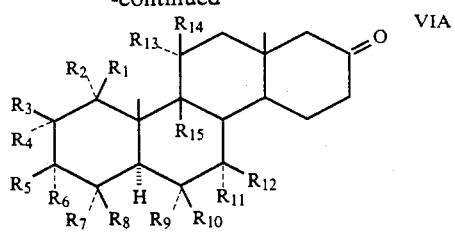

Nitrosation of the 17{-hydroxy 20-amine (XII) with nitrous acid in acid, such as acetic acid and the like affords the homoandrostanones of Formula VA and VIA.

In both of these reactions, the nitrous acid can be generated in situ, by techniques known to one skilled in the art, e.g., reacting a solution of sodium nitrite with acid, such as sufuric acid. The nitrosation reaction is normally effected at or near 0° C., although temperatures from about −78° C. to about room temperatures can be empolyed.

Alternatively, the 17-homoandrostane of Formula VA and VIA can be prepared by catalytic hydrogenation of IIIA and IVA, respectively using, e.g., palladium on carbon.

If substituents on the steroidal ring are themselves reactive under the reaction conditions, then these substituents can themselves be protected according to chemical techniques known in the art. A variety of protecting groups known in the art may be employed. Examples of many of these possible groups may be found in "Protective Groups in Organic Synthesis," by T. W. Green, John Wiley and Sons, 1981. For example, in the ring expansion reaction described hereinabove, if an hydroxy group is present on the ring, then said group can be converted to its methyl ether or to OTHP, and the like, which is stable under these conditions.

Compounds of Formulas IIIA, IVA, VA and VIA are useful intermediates in the preparation of other compounds of the present invention.

α-Alkylations

Alkylation on a position which is alpha to the ketone can be effected by procedures known to one skilled in the art. An illustrative sequence is described hereinbelow. Although the procedure outlined below depicts the reaction using 5α-homoandrostan-18-one as the substrate, the reactions are applicable to all of the intermediates produced hereinabove, namely IIIA, IVA, VA or VIA. For example,

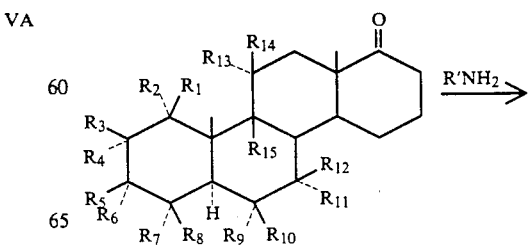

11

-continued

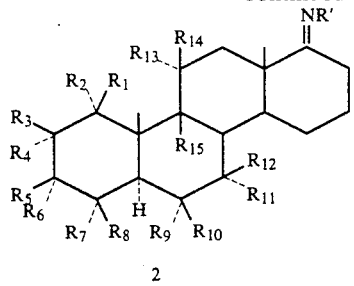

2

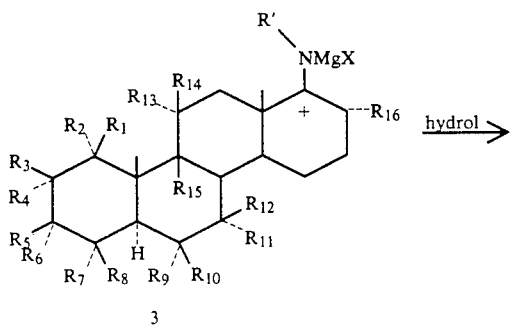

3

12

-continued

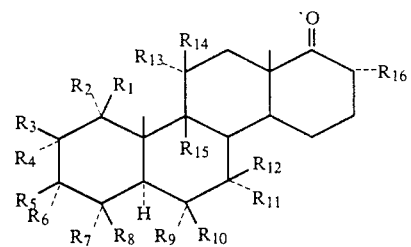

4

An intermediate such as 5α-homoandrostan-17a-one (VA), produced hereinabove reacts with a primary amine wherein R' is aryl, aralkyl or lower alkyl to form the corresponding imine (2). The imine is treated with a Grignard reagent, such as ethylmagnesium bromide in tetrahydrofuran to form the enamine salt. Alkylation of the enamine salt with an alkyl halide, wherein X is halide and $R_{16}$ is as defined hereinabove, according to the method of Stork and Dowd, JACS, 85, 2178 (1963) followed by hydrolysis, forms the alkyl-magnesium salt (3). Hydrolysis affords the products (4).

An Alternative procedure is shown hereinbelow.

Scheme 1

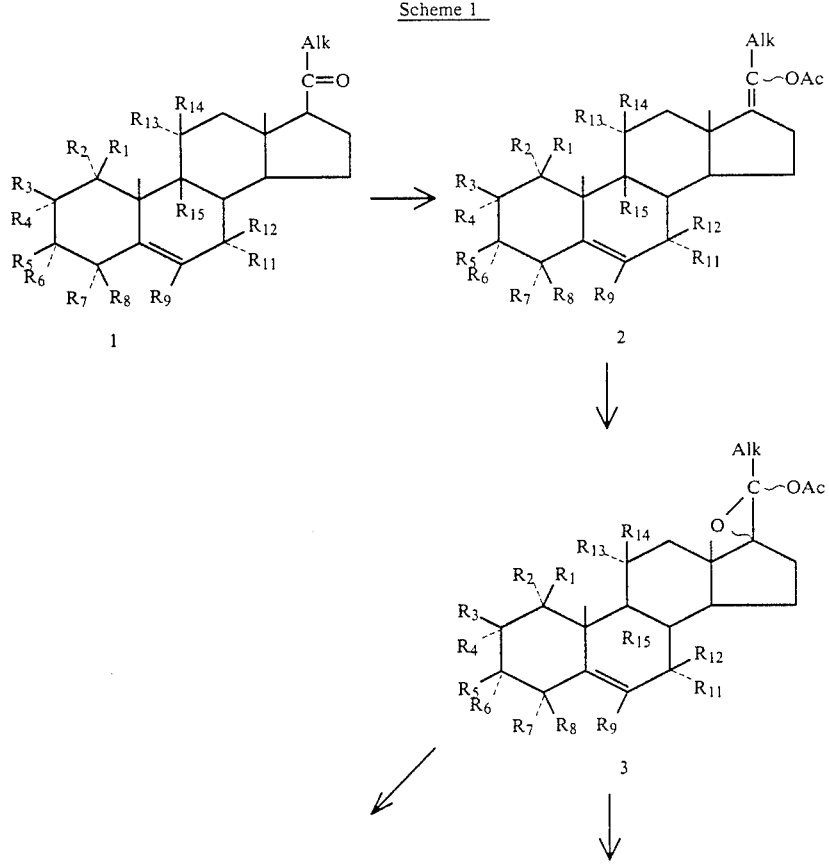

Scheme 1

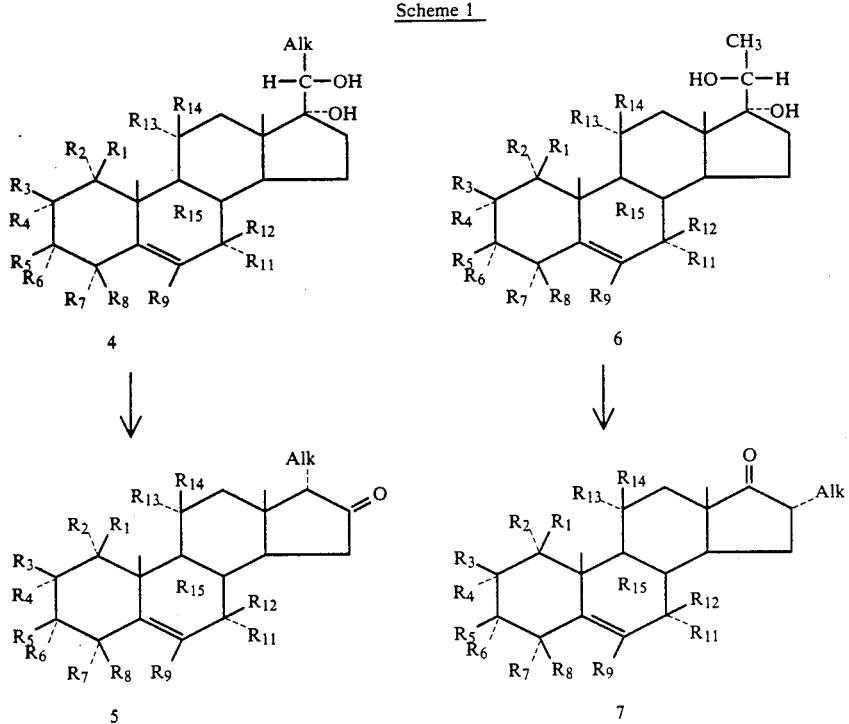

In the above-scheme, $R_1$-$R_9$, and $R_{10}$-$R_{14}$ are as defined hereinabove and alk is alkyl containing 1-6 carbon atoms in the principal chain and up to a total of 10 carbon atoms.

The 17 keto (5) and 17a-keto (7)-5-bromoandrostenes are prepared from known compounds or readily preparable intermediates using the procedure described by Williams et al. in *Journal of Organic Chemistry*, 30, 1447 (1965).

Enol acetylation of the steriod 1 using the procedures of Barton, et al. in Journal of Chemical Society of London, 747 (1954) gives 2. Treatment of 2 with peroxide, such as m-chloroperbenzoic acid gives 3. Reduction of 3 with a metal hydride, such as lithium aluminum hydride gives 4. Sequential saponification of 4 followed by sodium borohydride reduction gives 6, a diastereomer of 4. Solvolysis of 4 and 6 with potassium acetate affords the 17-keto (5)- and the 17a-keto (6)-5-homoandrostenes.

The corresponding homoandrostenes (13 and 15 of Scheme 2) can be synthesized by catalytic hydrogenation of 5 or 7, respectively.

Moreover, by substituting 5α-androstane derivative 9 for 1 in Scheme 1, 13 and 15 can also be prepared, as shown in Scheme II hereinbelow:

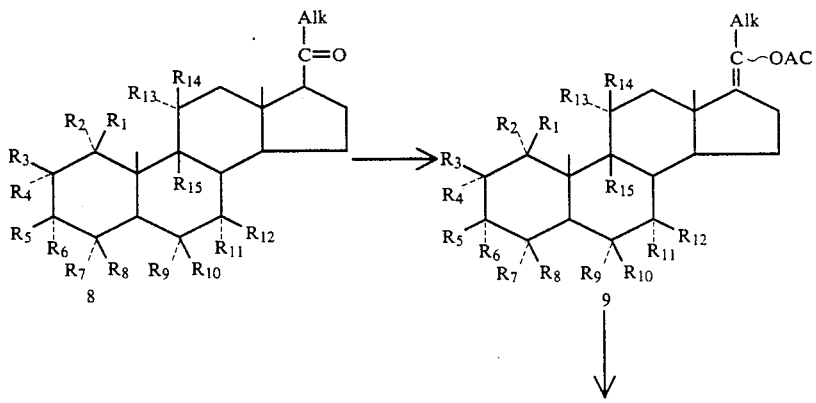

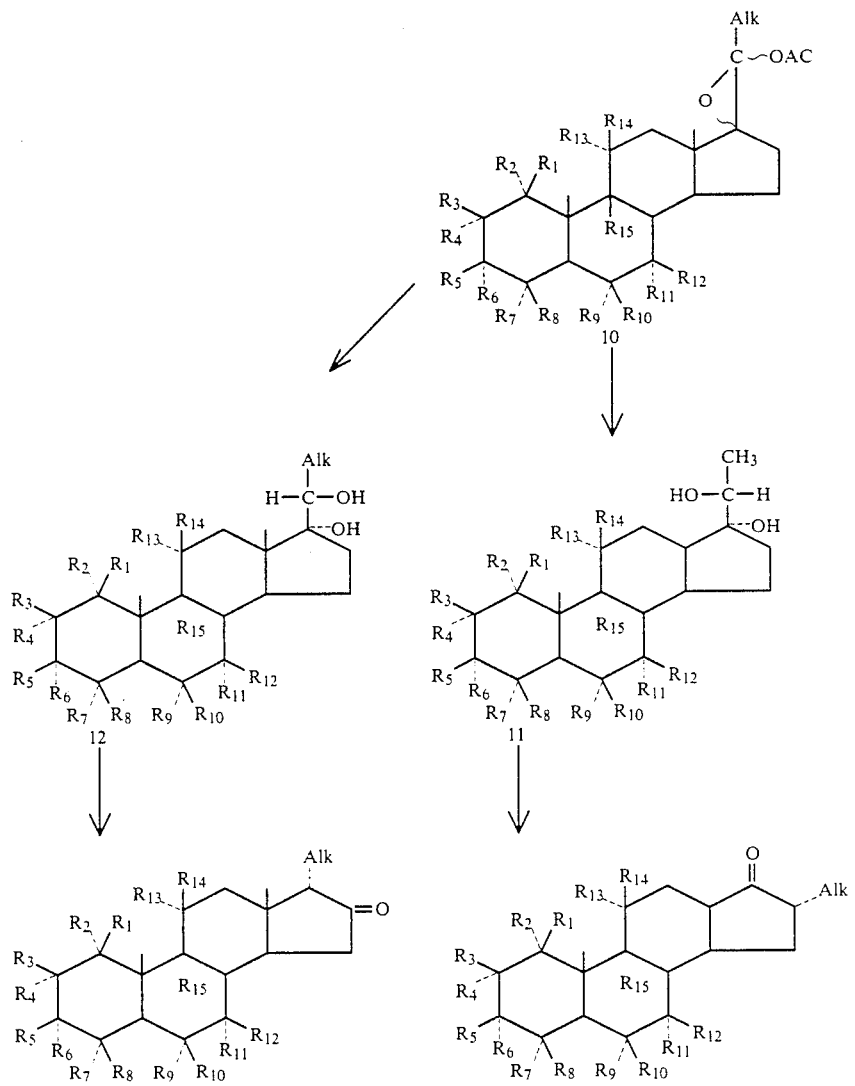

Any group on the ring that is reactive under the above conditions, e.g., alcohols, can be protected according to methods described in the art. A variety of protecting groups known in the art may be employed. Examples of many of these possible groups may be found in Protective Groups in Organic Synthesis" by T. W. Green, John Wiley and Sons, 1981. For example, an hydroxy group present on the ring can be protected by being converted to its methyl ether, which is stable under these reaction conditions.

Similarly, the 16 alkyl derivatives of IIIA, IVA and VIA can be prepared by this procedure:

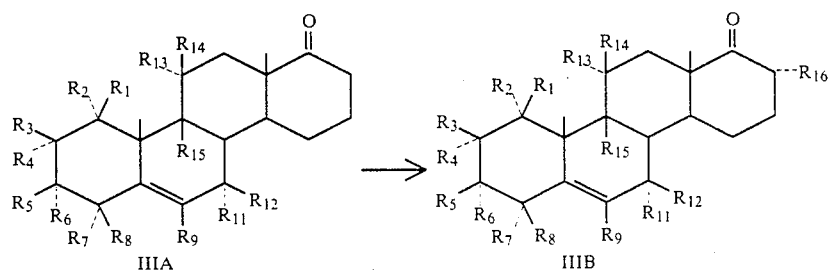

-continued

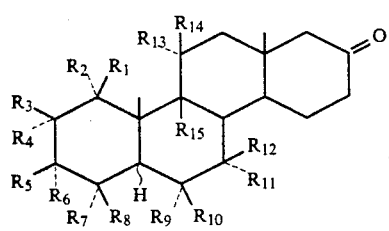

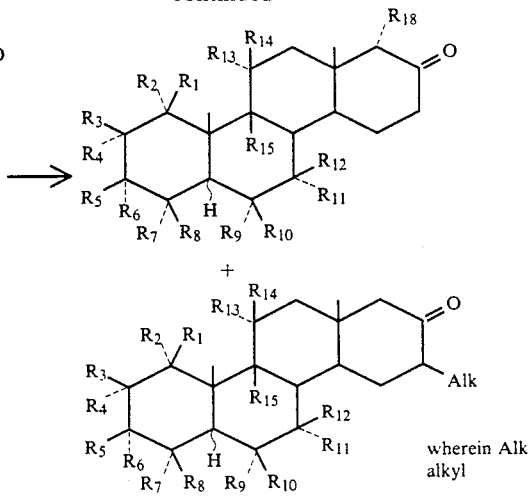

wherein Alk means alkyl

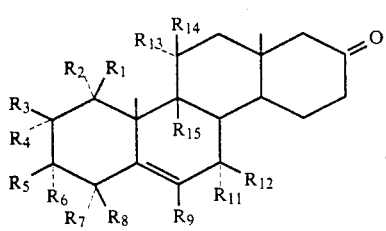

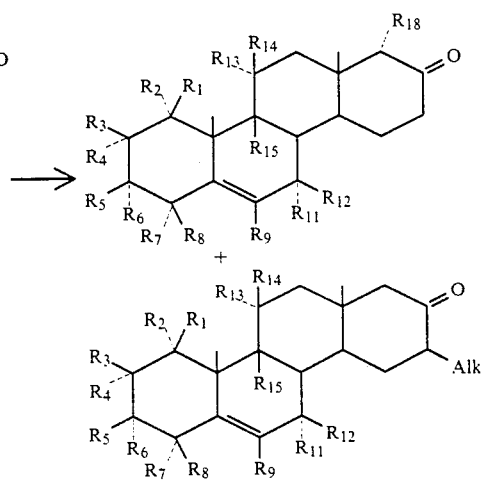

-continued

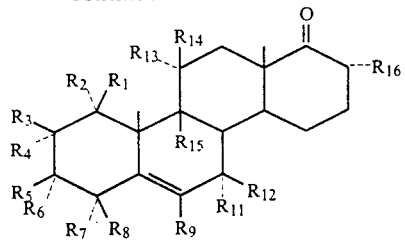

The alkylation of IIA and IVA produces both the 16-alkyl and the 17a-alkyl derivatives which can be isolated using separation techniques known in the art, e.g., chromatography.

An illustrative alternative procedure for 16 alkylation is illustrated below on IIIA. However, this procedure is also applicable on the other intermediates IV, VA and VIA produced hereinabove.

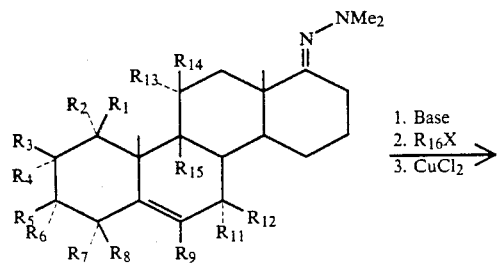

Alkylation of the ketodimethylhydrazone using a strong base, such as NaNH2, n-butyl lithium, and the like and an alkyl halide, $R_{16}X$, wherein X is a good leaving group such as halogen, mesylate tosylate and the like and $R_{16}$ is as defined hereinabove affords the 17α-alkylated steroid. Hydrazone cleavage with cuprous chloride in aqueous tetrahydrofuran leads to the regeneration of the $C_{17a}$ ketone. (2).

Similarly, the 16 alkyl derivative of IVA, VA and VIA can be prepared by the above method. As before, with respect to IVA and VIA, the corresponding 16 alkyl and 17a alkyl derivatives are formed, which can be separated by separation techniques, e.g., chromatography.

Another useful method is treating the keto steroid with a strong base, such as t-BuO, NaNH2, NaH, Et2-

NLi and the like. The resulting enolate anion is reacted with RX wherein R is lower alkyl and X is a good leaving group, such as halide, mesylate, tosylate and the like. The reaction is run in a solvent that will dissolve the reactants and in inert to both reactants and products as well. Typical solvents include but is not limited to 1,2-dimethoxyethane, THF, DMF and the like. Although the reaction below is illustrated for the 5α-homoandrostan-17a-one (VA) derivatives, the procedure is applicable for the alkylation of compounds IIIA, IVA and VIA:

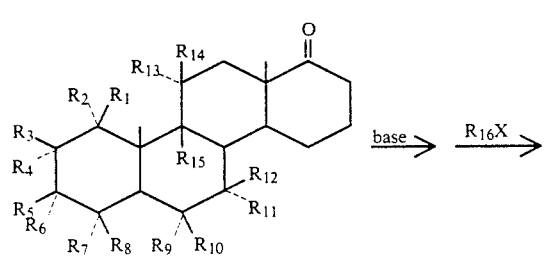

α-Halogenations

Halogenation on a position which is alpha to the ketone can be effected by procedures known to one skilled in the art. An illustrative reaction is depicted below:

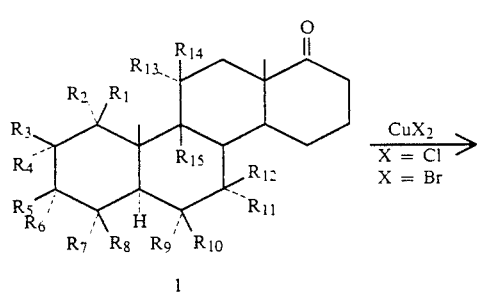

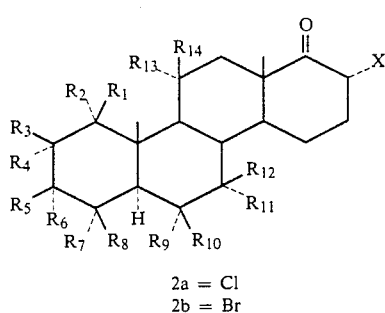

2a = Cl
2b = Br

Reaction of a steroidal ketone, such as homoandrostan-17-ones depicted hereinabove with cupric bromide yields the α-bromo derivative 2b. Similarly, reaction of 1 with cupric chloride according to the procedure of G. M. Kosower, et al. in J. Org. Chem. (1963), 28, 630, yields the α-chloride derivative 2a.

The α-fluoro derivative can be derived from the α-bromo or α-chloro derivatives made hereinabove. For example, reaction of the α-bromo ketone with lithium fluoride/18-Crown-6/Dimethyl sulfoxide affords both possible fluorides in the α-position to the carbonyl.

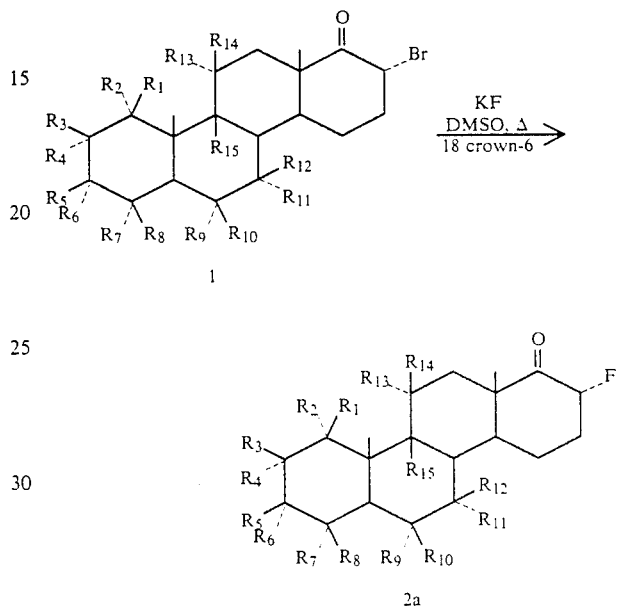

Alternatively, the α-fluoro compounds could be prepared by treating an enamide, e.g., the enamide of Formula I, with a fluorinating agent, such as perchloryl fluoride. Hydrolysis of the fluoro enamide acetate with aqueous acid gives 2a.

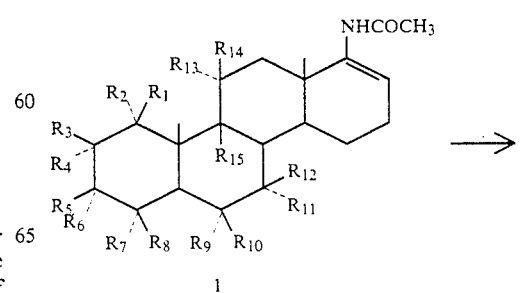

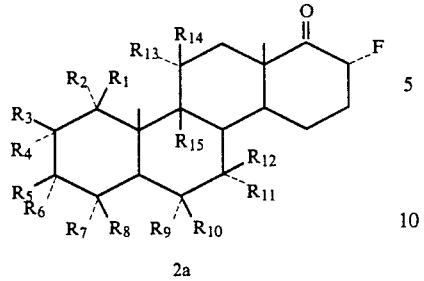

2a

The corresponding iodo compounds are formed from the reaction of the α-bromo or α-chloro steroidal ketone, e.g., 2b or 2a formed hereabove with refluxing sodium iodide in acetone. Both possible iodo products at the position are formed.

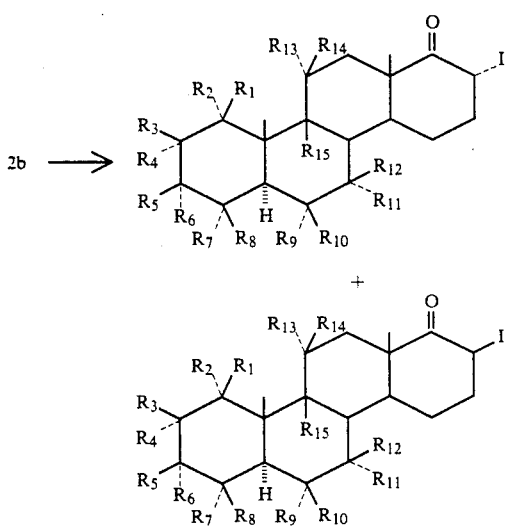

Although the reactions depicted hereinabove are only shown for the α-homoandrostan-17a-ones, the reactions are also applicable to the derivatives of IIIA, IVA and VIA formed hereinabove.

α-Hydroxylation

Hydroxylation on a position that is alpha to the ketone can be effected by procedures known to one skilled in the art. For example, the treatment of the α-halo homandrosten or α-halo homandrostanone with strong aqueous base, such as sodium hydroxide in aqueous pyridine yields the α-hydroxy steroidal ketone. See, M. Numazawa, M. Naqeoka, Y. Osawa, J. Org. Chem., 1982, 47, 4024. A procedure for the reaction is depicted hereinbelow using 17α-Bromohomoandrostan-17a-one, but is applicable with the other halo androstanone and α-halo androstenone derivatives described hereinabove.

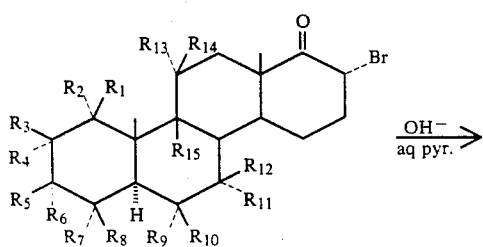

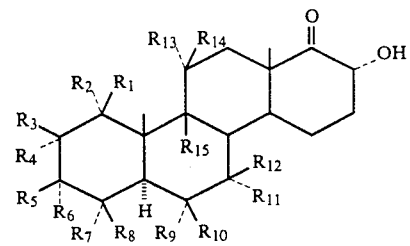

Alkoxylation

The alkoxy groups are derived from the corresponding alcohols. The alkoxy groups can be added to the starting materials prior to the ring enlargement or after the formation of the homo-androstan-17a-ones or homo-androsten-17a-ones. The methoxy substituent for example is formed by reacting the corresponding alcohol in methylene chloride with boron trifluoride and etheral diazomethane according to the procedure of Caserio, et al., JACS, 80, 2584 (1958). Similarly, the ethoxy substituent is formed by reacting the corresponding alcohol in methylene chloride with boron trifluoride and etheral diazoethane, generated in situ. Alternatively, the alkoxy substituents can also be added to the steroid ring by reacting the alcohol under Williamson reaction conditions with RX, where X is an organic leaving group such as halide tosylate or mesylate and R is loweralkyl. Any base normally employed to deprotonate an alcohol may be used, such as sodium hydride, sodium amide, sodium, sodium hydroxide, triethylamino or disopropyl ethylamine. Reaction temperatures are in the range of −78° C. to reflux. The reaction is carried out in a solvent that will dissolve both reactants and is inert to both reactants and products as well. Solvents include, but are not limited to, diethyl ether, tetrahydrofuran, N,N-dimethylformamide, methylene chloride, and the like.

The ketone should be protected with protecting groups known in the art. Examples of many of the possible protecting groups that may be utilized are found in "Protective Groups in Organic Synthesis," by T. W. Green, John Wiley and Sons, 1981. For example, the ketone may be protected as the ethyleneketal.

The following sequence is an illustrative of the Williamson synthesis for the preparation of the propyl ether derivative. However, the reaction is not limited to the reactants illustrated hereinbelow, and the general scheme can be utilized to prepare other alkoxy derivatives.

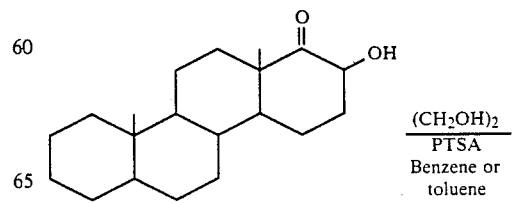

Ring Enlargement

Compounds of Formula XI and XIII in turn can be prepared according to the following sequence:

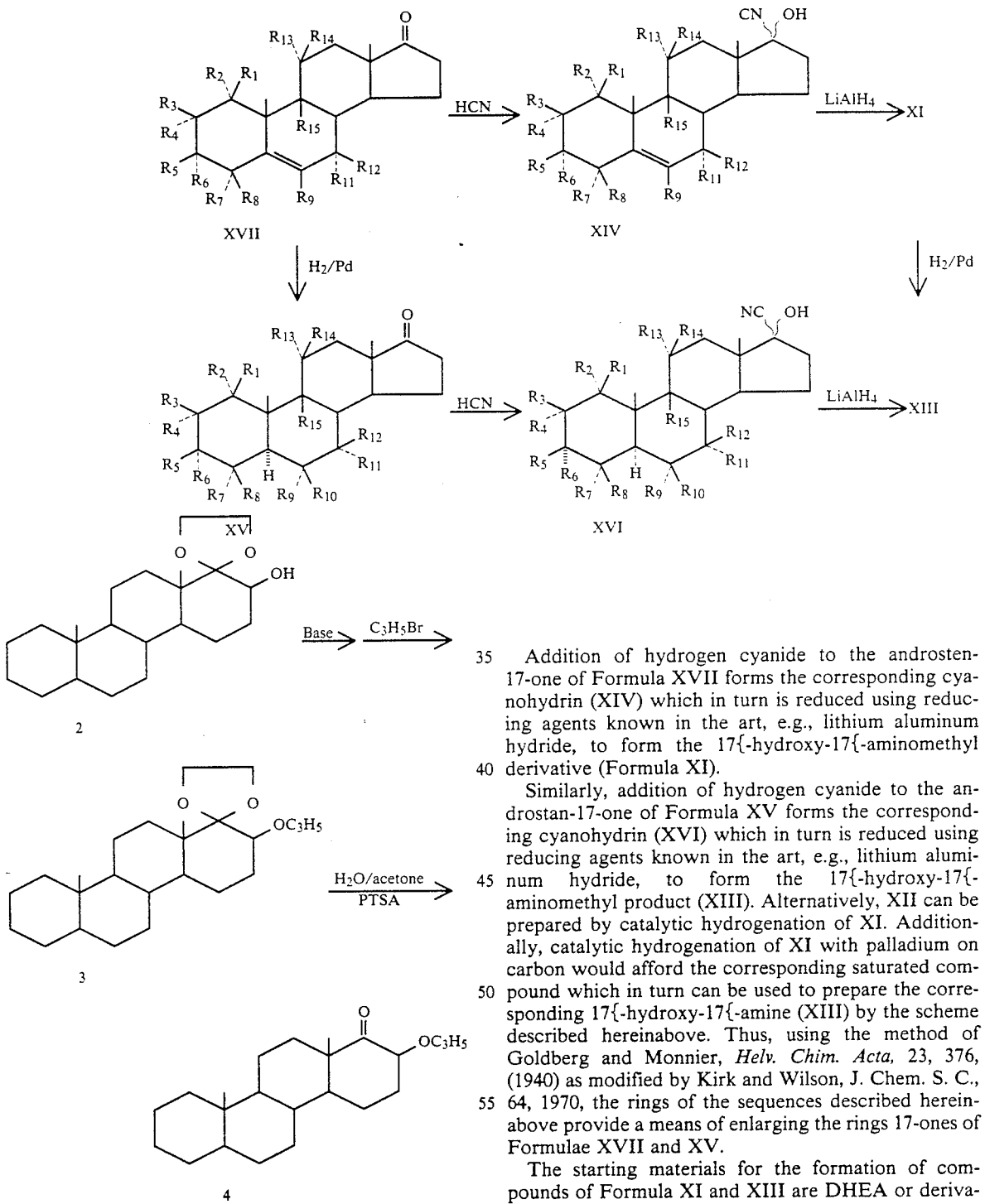

In the above sequence, the steroidal alcohol was ketalized to form the 17-hydroxy 5α-androstan-17a-one-17a-ethylene ketal 2. Said ethylene ketal was treated with base, such as sodium hydride and the resulting alkoxide is in turn reacted with propyl bromide to form the 17-propoxy-5α-androstan-17a-one-17a-ethylene ketal 3. Hydrolysis of the ketal affords the 17-propoxy-5α-androstan-17a-one 4.

Addition of hydrogen cyanide to the androsten-17-one of Formula XVII forms the corresponding cyanohydrin (XIV) which in turn is reduced using reducing agents known in the art, e.g., lithium aluminum hydride, to form the 17{-hydroxy-17{-aminomethyl derivative (Formula XI).

Similarly, addition of hydrogen cyanide to the androstan-17-one of Formula XV forms the corresponding cyanohydrin (XVI) which in turn is reduced using reducing agents known in the art, e.g., lithium aluminum hydride, to form the 17{-hydroxy-17{-aminomethyl product (XIII). Alternatively, XII can be prepared by catalytic hydrogenation of XI. Additionally, catalytic hydrogenation of XI with palladium on carbon would afford the corresponding saturated compound which in turn can be used to prepare the corresponding 17{-hydroxy-17{-amine (XIII) by the scheme described hereinabove. Thus, using the method of Goldberg and Monnier, *Helv. Chim. Acta*, 23, 376, (1940) as modified by Kirk and Wilson, J. Chem. S. C., 64, 1970, the rings of the sequences described hereinabove provide a means of enlarging the rings 17-ones of Formulae XVII and XV.

The starting materials for the formation of compounds of Formula XI and XIII are DHEA or derivatives thereof. The placement of the various substituents, i.e., $R_1$–$R_{15}$ as defined heretofore on the steroidal nucleus are outlined below. Although the various syntheses are described with respect to the substitution onto androsten-17-ones, the methods described hereinbelow can also be applied to the androstan-17-ones. Furthermore, the androstan-17-ones can be synthesized by catalytic hydrogenation of the corresponding androsten-17-ones.

Preparation of 3-Desoxy Compounds

The 3-desoxy compounds are prepared from the corresponding 3β-hydroxy compounds by techniques known in the art. For example,

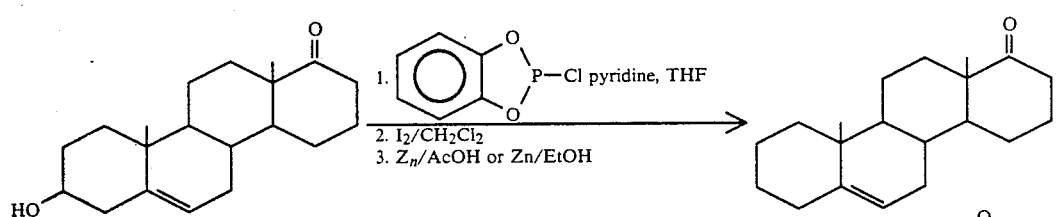

Using the above scheme, the 3-desoxy derivatives of IIIA, IVA, VA or VIA can be prepared.

Alkylation

Carbon-1-Alkylation

A representative procedure for alkylation at carbon-1 and specifically the synthesis of a 1α-methyl DHEA 3a and 1α-methyl-desoxy DHEA 3b is given in the Scheme below:

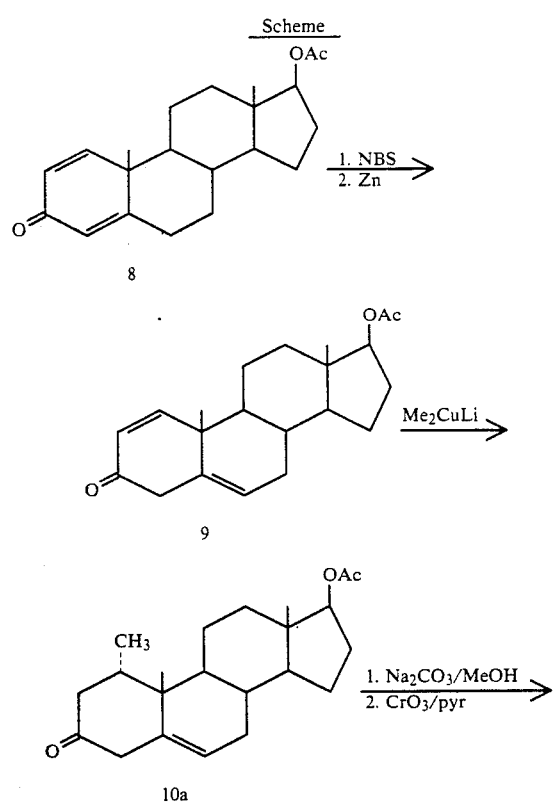

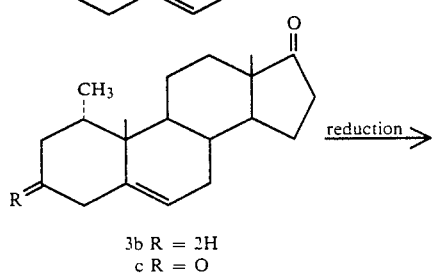

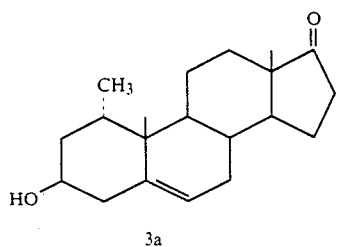

Allylic bromination (e.g. with N-bromosuccinimide (NBS) of 17β-acetoxyandrosta-1,4-dien-3-one 8 followed by treatment with zinc affords the non-conjugated enone 9. 1,4-Alkylation with lithiodimethyl cuprate provides the 1-αmethyl ketone 10a. At this stage the 10a may be converted to a methylene by Wolff-Kishner reduction or the Huang Minlon modification thereof. These vigorous reaction conditions result in the hydrolysis of the resulting carbon-17 acetate thereby yielding the hydroxy desoxy derivative, 17β-hydroxy-b 1α-methylandrost-5-ene (3b). Both 10a and its desoxy derivative can be converted via standard reactions, i.e., hydrolysis of the 17-acetate with sodium carbonate and methanol followed by chromium trioxide oxidation of the resulting 17-alcohol to the carbon-17 ketone. Selective reduction of the carbon-3 ketone, 3,17-diketone 3c using sodium borohydride/pyridine (pyr) yields 1α-methyl dehydroepiandrosterone 3a.

Alternatively, the 1α-methyl dehydropiandorsterone can be synthesized according to the following procedure:

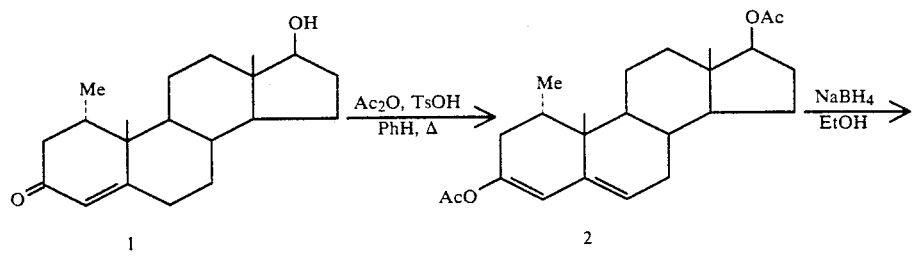

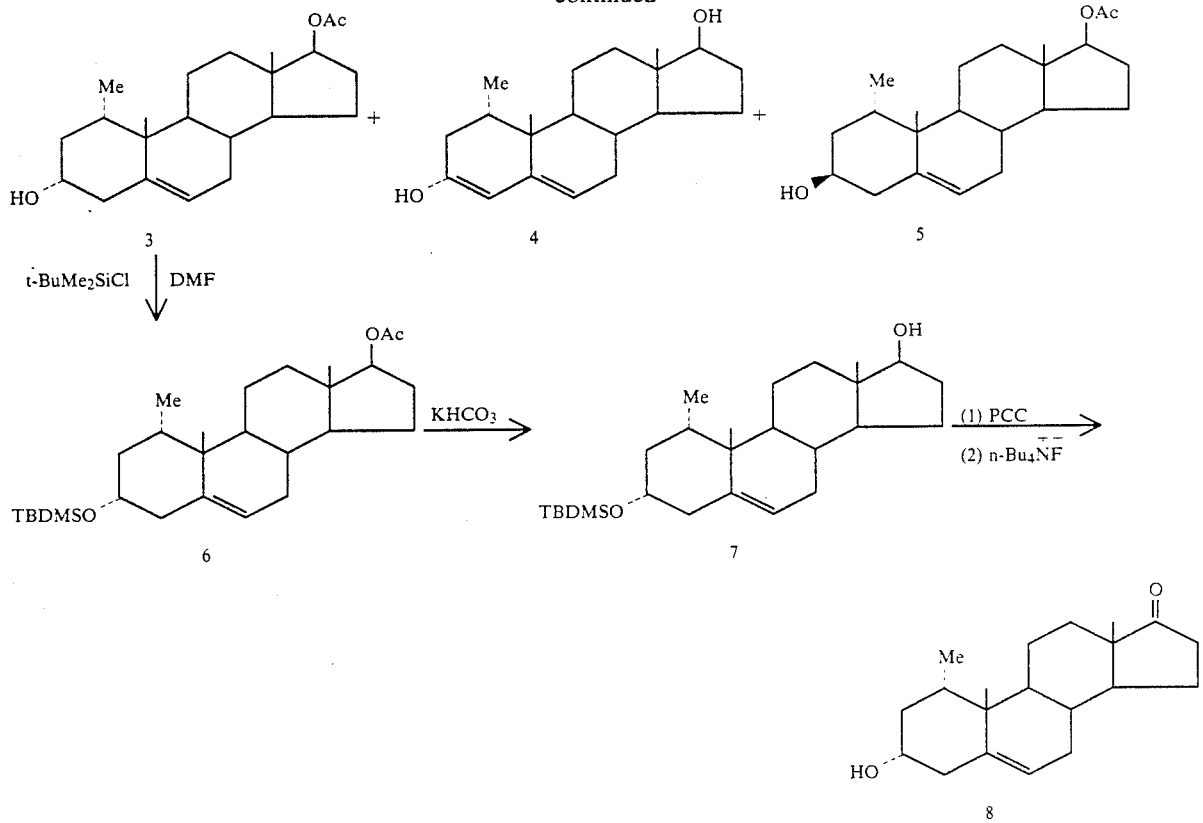

1α-methyltestosterone, 1, was reacted with acetic anhydride and p-toluenesulfonic acid in refluxing benzene, yielding the 3,5-dienol diacetate 2. Sodium borohydride reduction of 2 afforded 3α-hydroxy-17-acetate, 3 and 3α,17β-diol 4 and a small amount of 3β-hydroxy-17-acetate 5.

The 3-hydroxy group was protected with a protecting group known in the art. For example, 3 was converted to its t-butyldimethylsilyl ether 6 Hydrolysis of 6 with a base, such as potassium bicarbonate, in aqueous methanol afforded the 17β-hydroxy steroid 7. Pyridinium chlorochromate oxidation of the 17β-hydroxyl group followed by treatment with tetra n-butylammonium fluoride afforded the 3α-hydroxy-1α-methyl-androst-5-en-17-one.

Carbon-2-Alkylations

The following procedures are illustrative for alkylation at carbon-2 and are figuratively illustrated in the Scheme below.

Alkylation of testosterone (I) with an alkylating agent, such as methyl iodide, in the presence of a strong base, such as 2,2,6,6-tetramethyl lithium piperidide, lithium diethyl amide, lithium diisopropylamide (LDA), triphenylmethyl lithium, n-butyl lithium and the like gives a mixture of the 2α and 2β-alkyl-17β-hydroxy-4-androsten-3ones (2 and 3). Treatment of the mixture with a strong base, such as sodium methoxide in methanol, epimerizes the 2β-axial alkyl to the 2-α-equitorial configuration (2). Acetylation of 2 with an acetylating agent, such as acetic anhydride (Ac₂O) and p-toluenesulfonic acid (p-TSA) in toluene afforded 2α-methyl-3,17β-dihydroxy-3,5-androstadien-3,17-diacetate (4). Treatment of the diacetate (4) with sodium borohydride in 95% ethanol yielded 2α-methyl-3β,17β-dihydroxy-5-androsten-17-acetate (5). Protection of the 3-hydroxy group as a tetrahydropyranyl ether followed by hydrolysis of the 17-acetate yielded 2α-methyl-3β,17β-dihydroxy-5-androsten-3-tetrahydropyranyl ether 7. Oxidation of the C-17 hydroxy group in 7 followed by hydrolysis of the tetrahydropyranyl ether with hydrochloric acid and aqueous acetone yielded 3β-hydroxy-2α-methylandrost-5-en-17-one (9).

The following is a specific example for the synthesis of 2α-methyl DHEA.

To a solution of diisopropylamine (5.3 ml, 38 mmol) in freshly distilled tetrahydrofuran (80 ml) stirred at −78° C. was added n-butyllithium (29.3 ml of 1.3M in hexane, 38 mmol). This was stirred at −78° C. for 30 minutes then warmed to −30° C. and 17β-hydroxy-4-androsten-3-one (1) (5.0 g, 17.3 mmol) in tetrahydrofuran (30 ml) was added dropwise. After 30 minutes at −30° C. iodomethane (4 ml, 80 mmol) was added. The mixture was allowed to slowly warm to room temperature with stirring, then saturated ammonium chloride solution was added and the product was extracted with ether. The organic layer was dried and the solvent removed to give a mixture of isomers 2 and 3 as an oil (5.26 g) which was used in the next step.

To a stirred solution of sodium (0.75 g, 32 mmol) dissolved in methanol (100 ml) was added the epimeric mixture of 2-methyl-17β-hydroxy-4-androsten-3-one, 2 and 3 (4.93 g, 16.2 mmol) in methanol (100 ml). After 17 hours at room temperature, saturated ammonium chloride solution was added and most of the solvent was removed to give a gum (4.86 g) which was purified by column chromatography on silica gel. Elution with hexane/ether gave 1.6 g of 2 which crystallized from methanol mp 149°–151° C.; H¹ NMR (CDCl₃) δ5.64 (s, 1, H-4), 3.60 (t, 1, H-17, J=9Hz), 1.24 (s, 3, H-19), 1.13

(d, 3, H-2 methyl, J=6 Hz), 0.83 (s, 3, H-18); MS m/e 302 (M+, 33), 260 (21), 246 (29), 28 (100).

A solution of 2α-methyl-17β-hydroxy-4-androsten-3-one (2) (4.86 g, 16.1 mmol) product mixture from the previous step in acetic anhydride (40 ml) and paratoluene sulfonic acid (200 mg) in toluene (100 ml) was refluxed 3½ hours. Pyridine (1 ml) was added, and the mixture was concentrated on a rotary evaporator, then partitioned between methylene chloride and water. The organic layer was dried and the solvent removed. The product mixture (5.78 g) was separated on a flash silica column to give 2α-methyl-3,5-androstadien-3,17βdioldiacetate (4) 1.81 g (27.4%) crystallized from Et₂O-hexane mp 170°-171° C.

H¹ NMR (CDCl₃) δ5.57 (s, 1, H-4), 5.40 (m, 1, H-6), 4.55 (t, 1, H-17, J=9Hz), 2.08 (s, 3, 3-acetate), 2.01 (s, 3, 17-acetate), 1.06 (s, 3, H-19), 0.98 (d, 3, 2-methyl, J=6 Hz), 0.83 (s, 3, H-18); MS m/e 386 (M+, 3) 358 (12), 43 (100).

A suspension of 2α-methyl-3,5-androstadien-3,17β-dioldiacetate (4) (1.31 g, 3.4 mmol) and sodium borohydride (1.3 g) in 95% ethanol (100 ml) was stirred at room temperature for 3½ hours. The solution was cooled to 0° C. and glacial acetic acid was added, followed by saturated sodium bicarbonate solution. The product was partitioned between dichloromethane and water, the organic layer dried, and the solvent removed to give 1.23 g product mixture which was separated on 40 g of flash silica column eluted to give 5, 0.7 g (from ether hexane) mp 179°-182° C.;

¹H NMR (CDCl₃) δ5.27 (m, 1, H-6), 4.62 (t, 1, H-17, J=9Hz), 3.03 (t, 1, H-3, J=9Hz) 2.05 (s, 3, 17-acetate), 1.07 (s, 3, H-19), 1.02 (d, 3, 2-methyl, J=8Hz), 0.83 (s, 3, H-18).

A solution of 2α-methyl-3β,17β-dihydroxy-5-androsten-17-acetate 5 (1.42 g, 4.1 mmol) dihydropyran (DHP) (10 ml) and paratoluene sulfonic acid (100 mg) in ether (50 ml) was stirred at room temperature for 17 hours. The ether solution was washed with saturated sodium bicarbonate solution, then water, and dried, and the solvent was removed to give the product mixture as an oil (1.65 g). The product was not purified but carried on to the next step.

2α-Methyl-3β,17β-dihydroxy-androst-5-ene-3-tetrahydropyranyl ether 17-acetate, 6, from the previous step (1.65 g, 3.84 mmol) was dissolved in a solution of 5% potassium carbonate in 4:1 methanol:water (100 ml) and refluxed 1.5 hours. Most of the solvent was removed under reduced pressure and the product was partitioned between chloroform and water. The organic layer was dried and solvent removed to give 1.45 g of the product 7 which was used in the next step.

The product mixture 7 from the previous step (1.45 g, 3.84 mmol) was dissolved in pyridine (10 ml) and added to the complex formed by mixing chromium trioxide (2 g) in pyridine (20 ml). This was stirred 2½hours at room temperature, then 1:1 ether:benzene (30 ml) was added and the mixture was filtered through celite then silica gel. The solvent was removed to give the product mixture 8, 1.52 g as an oil, which was carried on to the next step.

A solution consisting of the product mixture 8 from the previous step (1.52 g, 3.94 mmol) and 3N HCl (2 ml) in acetone (40 ml) was stirred at room temperature for 3 hours. Saturated sodium bicarbonate solution was added and the product was extracted with dichloromethane. The organic layer was dried and the solvent removed to give 1.17 g product mixture which was separated on a flash silica column. Elution with 30:70 ether:hexane gave 3β-hydroxy-2α-methyl-androst-5-en-17-one (9) (317 g) which was crystallized from ether:hexane mp 171.5–173;

H¹ NMR(CDCl₃) δ5.45 (m, 1, H-6), 3.10 (broad m, 1, H-3), 1.13 (s, 3, H-19), 1.07 (d, 3, 2-methyl, J=8Hz), 0.97 (s, 3, H-18).

As stated before, the above reactions involving alkylation at carbon-2 are figuratively illustrated in the Scheme hereinbelow.

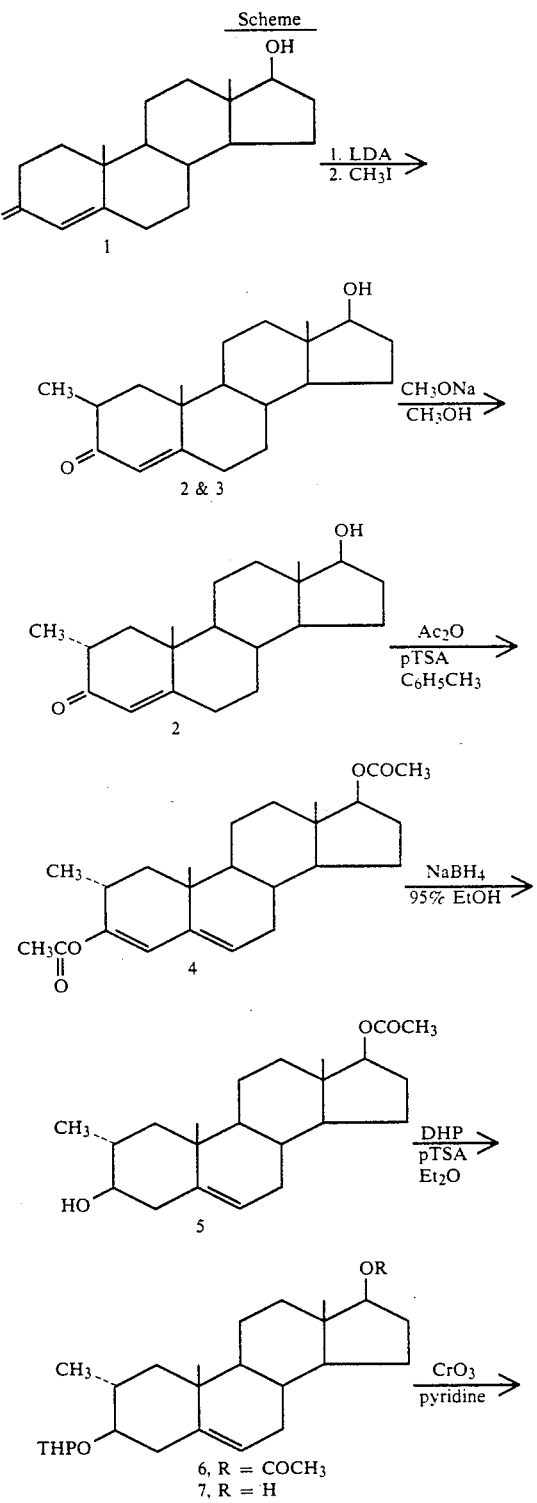

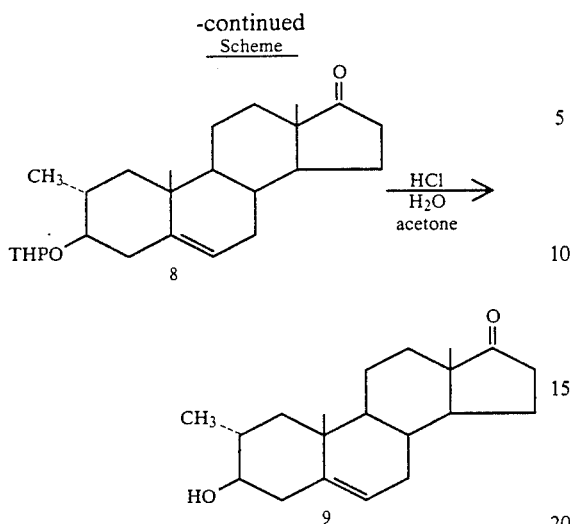

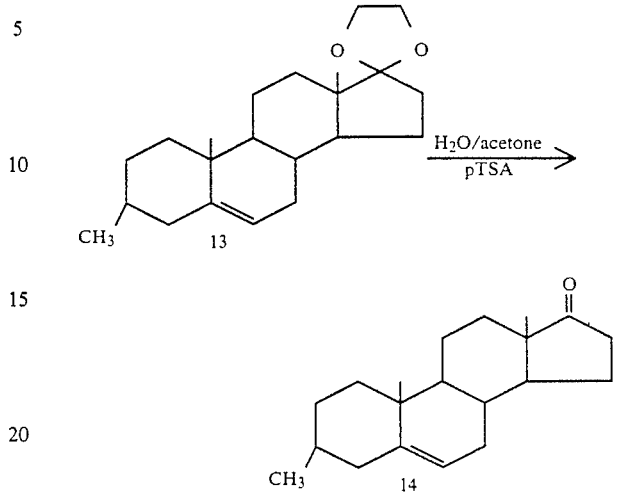

Carbon 3-Alkylations

The schematic for carbon 3-alkylations are shown figuratively in the scheme below.

Synthesis of dehydroepiandrosterone with a methyl group replacing the hydroxy group at carbon-3 is shown below in the Scheme hereinbelow. The methyl configuration at Carbon-3 is $\beta$, as determined by X-ray analysis. 3$\beta$-Hydroxy-5-androst-en-17-one (10) was iodinated at carbon-3 with 0-phenylenephosphoro-chloridite followed by decomposition of the resulting phosphite ester with iodine. 3$\beta$-Iodoandrost-5-en-17-one (11) was ketalized, then alkylated with a mixture of methyl lithium and cuprous cyanide in tetrahydrofuran to yield 3$\beta$-methylandrost-5-en-17-ethylene ketal (13). Hydrolysis of the ketal afforded 3$\beta$-methylandrost-5en-17-one (14).

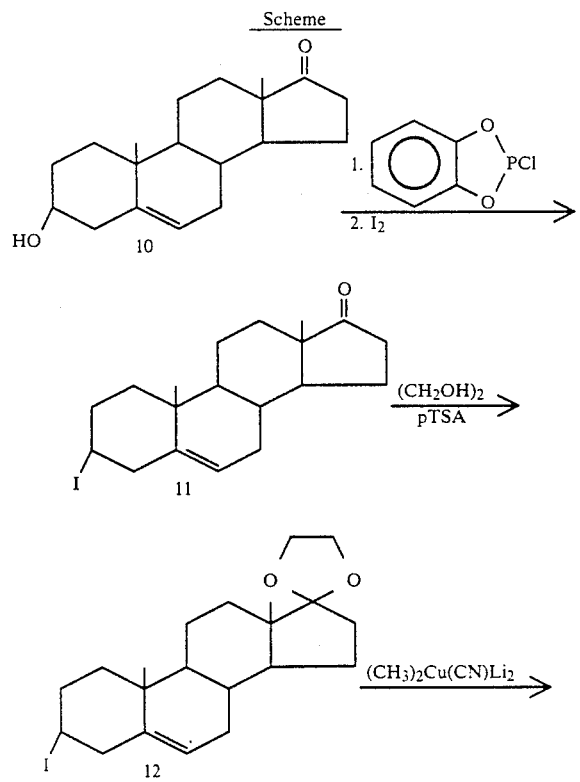

More specifically, 3$\beta$-iodoandrost-5-en-17-one (11) (11.83 g, 29.7 mmol), ethylene glycol (20 ml) and p-toluene sulfonic acid (200 mg) in benzene (250 ml) were refluxed under a Dean Stark trap for 72 hours. The solution was washed with saturated sodium bicarbonate, water, then dried over magnesium sulfate. Evaporation and recrystallization from ether afforded 11.5 g (87.3%) of 3 $\beta$-iodoandrost-5-en-17-one-17-ethyleneketal (12): mp 140°–141° C., IR(KBr): 3010, 2940, 1470, 1425, 1375 cm$^{-1}$; $^1$H NMR (CDCl$_3$) $\delta$5.44 (brd J=6Hz, 1H, H-6), 3.91 (s, 4H, ketal), 1.07 (s, 3H, C-19 Me), 0.88 (s, 3H, C-18 Me); MS (m/e): 442 (M$^+$, 1), 380 (35), 315 (57), 253 (67), 227 (11), 105 (24), 99 (100), 91 (35), 55 (27), 41 (33).

Cuprous cyanide (4.465 g, 49.9 mmol) was placed in a dry 500 ml 3 neck round bottom flask equipped with a magnetic stirrer. The system was flushed with N$_2$, and dry THF (30 ml) was added. The suspension was cooled to $-78°$ C. and MeLi solution, 1.5M (66.5 ml, 99.8 mmol), was added via a syringe. The solution was allowed to warm to 0° C. for 5 min., which resulted in a clear tan solution.

After recooling to $-78°$ C., the 3$\beta$-iodo-17-ketal (3) (7.35 g, 16.6 mmol) in 40 ml dry tetrahydrofuran was added via a syringe, and the solution was allowed to warm to room temperature and was stirred for 18 hours under N$_2$. The solution was extracted with 100 ml of 90% saturated NH$_4$Cl/10% conc. NH$_4$OH. The organic layer was separated, dried over MgSO$_4$ and evaporated to give 6.69 g of crude product. Chromatography on flash silica (240 g) and elution with 1% Et$_2$0/99% hexane gave 6.41 g of colorless crystals. Recrystallization from methanol (200 ml) gave 3$\beta$-methylandrost-5-en-17-one 17-ethyleneketal. mp 121°–122° C.

Anal. Cal. C 80.06, H 10.38.
Found C 80.12, H 10.55.
IR(KBr) 3010, 2930, 1450, 1430, 1370 cm$^{-1}$; $^1$H NMR (CDCl$_3$): $\delta$5.33 (brd J=6Hz, 1H, H-6), 3.90 (s, 4H, ketal), 1.03 (s, 3H, C-19 Me) 0.91 (s, 3H, C-18 Me); 0.97 (d, 3H, C-3 Me); MS (m/e): 330 (M$^+$, 16), 316 (7), 268 (29), 253 (22), 239 (9), 99 (100), 91 (22), 55 (27), 41 (22).

The 3$\beta$-methylandrost-5-en-17-one 17-ethylene ketal (13) (2.20 g 6.7 mmol) was dissolved in acetone (100 ml).

p-Toluenesulfonic acid (100 mg) and H₂O (20 ml) were added and the solution was refluxed for 2 hours. The solution was evaporated, taken up in ether (30 ml), washed with saturated NaHCO₃, H₂O, and then dried over MgSO₄. The solution was filtered and evaporated to give a colorless solid which was recrystallized from methanol to give 3β-methylandrost-5-en-17-one (14) as colorless plates, 1.17 g (61%) mp 148°–150° C.; IR(KBr) 3010, 2910, 1740, 1455, 1430, 1365 cm⁻¹; ¹H NMR (CDCl₃) δ5.41 (brd, J=6Hz, 1H, H-6), 1.11 (s, 3H, C-19 Me), 0.99 (s, 3H, C-18 Me), 1.07 (d, 3H, C-3 Me); MS (m/e) 286 (M+, 58), 271 (51), 229 (31), 159 (36), 105 (72), 9! (95), 79 (89), 55 (9), 41 (100).

Anal. Calc. C 83.85, H 10.55
C 83.66, H 10.65.

Similarly, by using the appropriate starting materials, the following compounds were also prepared:

3β-Ethylandrost-5-en-17-one (91%)

mp 73°–75° C.; NMR (CDCl₃) δ5.31 (br s, 1H, H-6), 0.99 (s, 3H, C-19 Me), 0.88 (s, 3H, C-18 Me); IR (KBr) 2910, 1735, 1435, 1365, 1010; MS 300 (M+, 100), 285 (68), 272 (85), 267 (130, 257 (38), 250 M* (285–267), 215 (25), 203 (53); Anal. Calcd for C₂₁H₃₂O; C, 83.93; H, 10.74. Found: C, 83.73; H, 10.85.

3β-n-Propylandrost-5-en-17-one (80%)

mp 103°–105° C.; NMR (CDCl₃) δ5.3 (br s, 1H, H-6), 1.01 (s, 3H, C-19 Me), 0.87 (s, 3H, C-18 Me), 2.5–1.0 (m, complex); IR (KBr) 2900, 1735, 1445, 1365, 1070; MS 314 (M+, 49), 299 (4), 272 (2), 255 (37), 238 (36), 229 (39), 215 (15), 99 (100); Anal. Calcd for C₂₂H₃₄O; C, 84.01; H, 10.89. Found: C, 83.99; H, 10.63.

3β-n-Butylandrost-5-en-17-one (82%)

mp 84°–86° C.; NMR (CDCl₃) δ5.31 (br s, 1H, H-6), 0.98 (s, 3H, C-19 Me), 0.87 (s, 3H, C-18 Me), 2.5–1.0 (m, complex); IR (KBr) 2900, 1735, 1450, 1370, 1015; MS 328 (M+, 8), 313 (5), 272 (100), 255 (47), 238 (15), 229 (10), 215 (31), 203 (45); Anal. Calcd for C₂₃H₃₆O: C, 84.08; H, 11.04. Found: C, 83.96; H, 11.12.

Alkylation at Carbon 4

A procedure for carbon-4 alkylation and the synthesis of 4α-methyl DHEA is given in the Scheme below.

Scheme

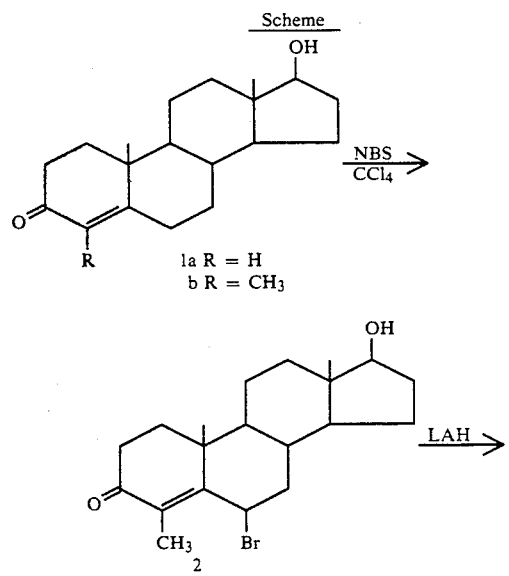

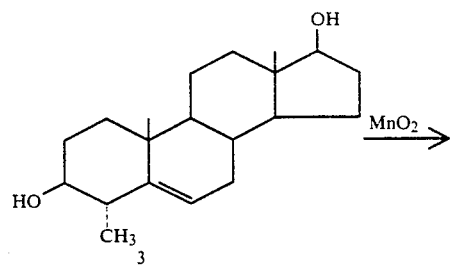

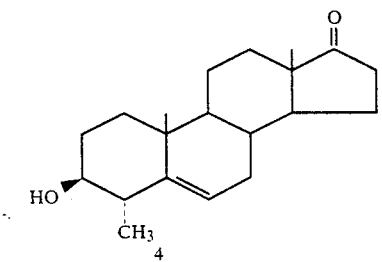

With reference to the Scheme above, alkylation of testesterone 1a using potassium t-butoxide and methyl iodide yielded 4-methyltestosterone 1b. Allylic bromination of 4-methyltestosterone using N-bromosuccinimide in carbon tetrachloride yields the 6β-bromo-4-methylandrost-4-en-17β-ol-3-one 2. Lithium aluminum hydride reduction and loss of bromide yields 3, according to the method of Knapp and Schroepfer, *J. Org. Chem.* 1974, 39, 3247. Selective manganese dioxide oxidation of 3 affords 3β-hydroxyl-4α-methylandrost-5-en-17-one.

Alkylation at Carbon-6

Steroids may be alkylated at carbon-6 using the method of U. Stache and W. Fritsch, Liebigs Analen 1966, 697, 204.

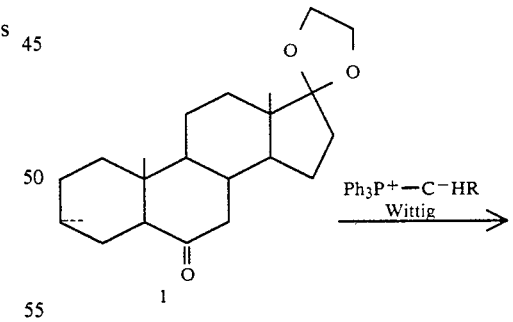

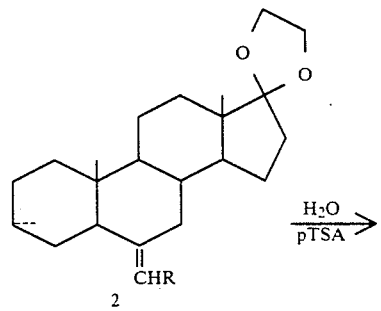

35
-continued

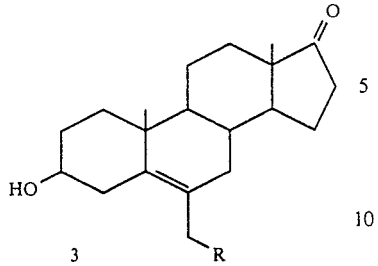

3α,5-Cyclosteroids such as 3α,5-cyclo-5α-androstan-6,17-dione 17 ketal 1 are readily available by solvolysis of steroidal 5-ene-3β-tosylates and mesylates followed by oxidation of the C-6 hydroxy group. Methylenation of 1 affords 6-methylene-3α,5-cyclo-5α-androstan-17-one 17-ketal 2 (R=H). Treatment of 2 with aqueous acid results in the addition of water and the formation of 3β-hydroxy-6-methylandrost-5-en-17-one, 3 (R=H).

Alkylation at C-7

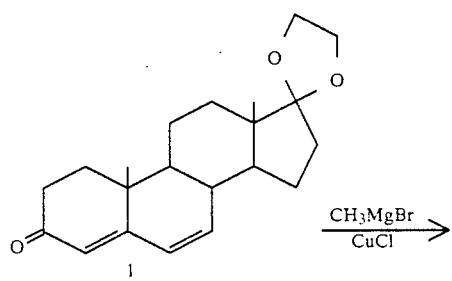

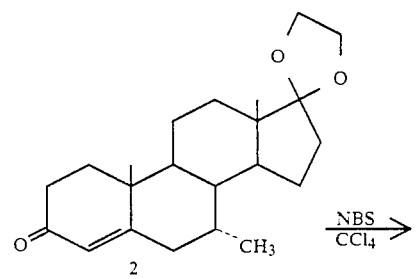

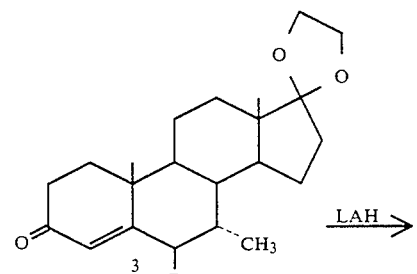

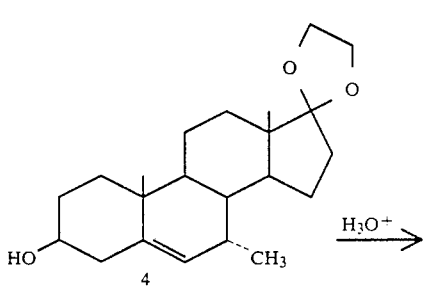

36
-continued

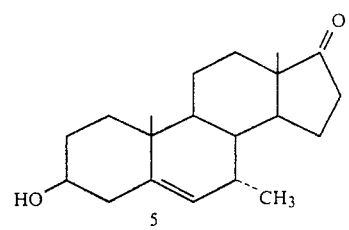

Alkylation of androsta-4,6-dien-3,17-dione 17 ketal 1 with methyl magnesium bromide in the presence of cuprous chloride, proceeds via conjugate addition to yield 7α-methylandrost-5-en-3,17-dione 17 ketal 2. Allylic bromination of 2 using N-bromosuccnimide in carbon tetrachloride yields the 6β-bromo-7α-methylandrost-4-en-3,17-dione 17 ketal 3. Lithium aluminum hydride reduction of the ketone in 3 with concomitant double bond migration and loss of bromide should yield 4. Deprotection of the C-17 ketone with aqueous acid yields 3β-hydroxy-7α-methylandrost-5-en-17-one, 5. Higher homologues may be synthesized using the substituted Grignard reagent i.e. R=CH₃, C₂H₅, C₃H₇. The 7β-epimer can be synthesized by treatment of 2 with DDQ--dichlorodicyanoquinone to generate another olefin at C-7. Catalytic reduction of this olefin should occur from the α face of the steroid to yield the 7β-methyl steroid i.e. 7β-methylandrost-5-en-3,17-dione 17 ketal. Following the same sequence as above yields 3β-hydroxy-7β-methyl-androst-5-en-17-one.

Alkylation at Carbon-11

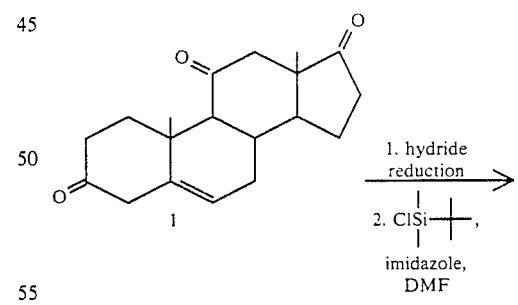

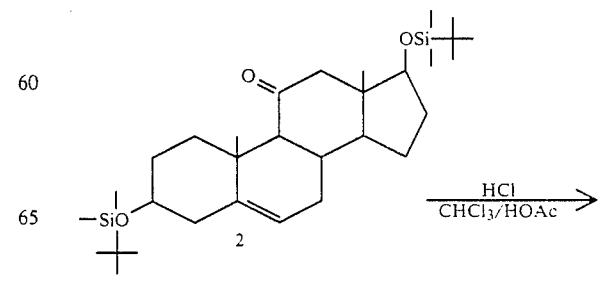

-continued

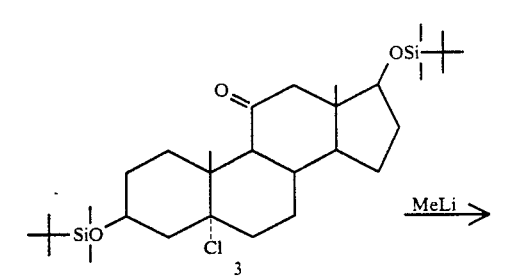

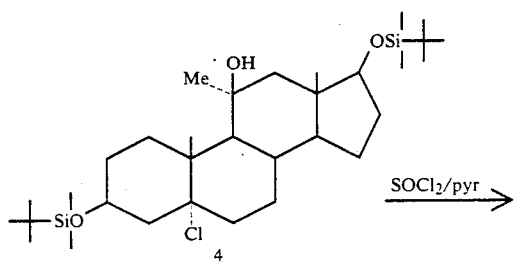

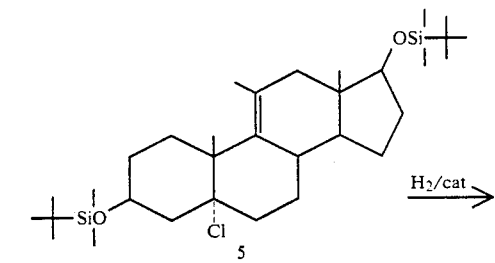

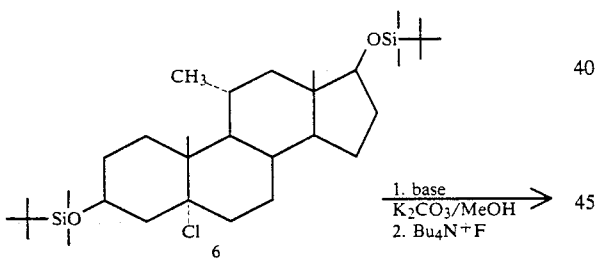

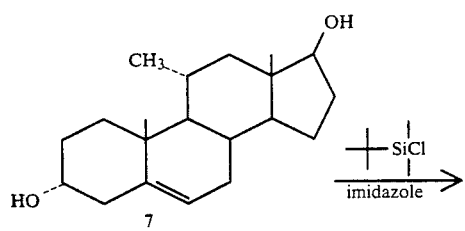

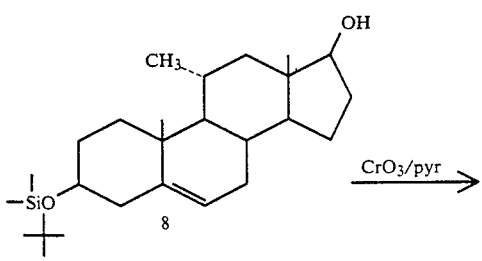

-continued

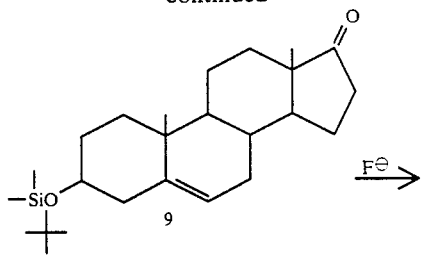

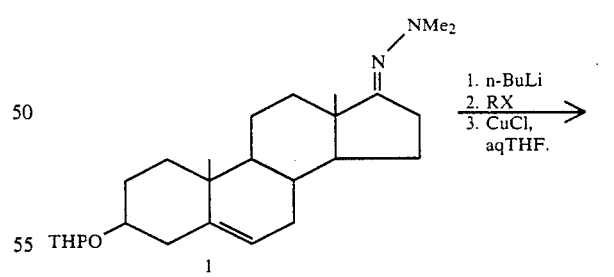

Due to the hundred nature of the C-11 ketone, selective reduction of androst-5-en-3,11,17-trione 1 with hydride should yield the C-3, C-17 dihydroxy steroid 2a, R=H which is protected as its bis(dimethyl-tert-butylsilyl)ether 2b R=Si(CH₃)₂t-Bu. Addition of hydrogen chloride across the C-5 olefin affords 5α-chloro-3β,17β-dihydroxyandrost-5-en-11-one 3,17-bis(dimethyl-t-butylsilyl) ether 3. Alkylation with methyl lithium proceeds from the less hindered α face to yield 5α-chloro-11α-methylandrostan-3β,11β,17β-triol-3,17-bis(dimethyl-t-butylsilyl) ether 4. Dehydration of the methylcarbinol 4 with thionyl chloride in pyridine provides the olefin 5. Catalytic hydrogenation of 5 gives the saturated 11α-methyl-5αchloro-bis (silyl) ether 6. Treatment of the chloro silyl ether 6 with base followed by tetrabutyl ammonium fluoride affords 11α-methylandrost-5-en-3β,17β-diol 7. Selective silylation yields 11α-methylandrost-5-en-3β,17β-diol 3-dimethyl t-butylsilyl ether 8. Oxidation of the C-17 alcohol in 8 yields 9 and deprotection of the 3-alcohol yields 11α-methylandrost-5-en-3β-ol-17-one 10. (11α-methyl DHEA).

Alkylation at Carbon-16

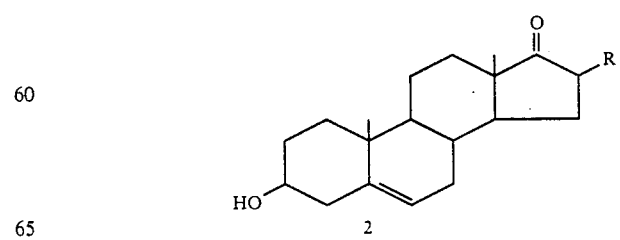

Alkylation of the 17-ketodimethylhydrazone of DHFA 3-tetrahydropyranyl ether using n-butyl lithium as the base followed by an alkyl halide RX, afforded the 16α-alkylated steroid. Hydrazone cleavage with cuprous chloride in aqueous tetrahydrofuran led to regeneration of the C-17 ketone and concomitant cleavage of the tetrahydropyranyl ether resulting in the 16α-alkyl-3β-hydroxy-androst-5-en-17-one 2.

The following procedure is illustrative for the preparation of 16-methyl derivatives of 3β-methyl-5-androsten-17-ones.

As shown supra, 3β-methyl-5-androsten-17-one 2 was prepared from DHEA (1).

Treatment of 2 with lithium diisopropylamide in tetrahydrofuran at −78° C. generated an enolate which was smoothly alkylated with excess methyl iodide to afford 3β,16α-dimethylandrost-5-en-17-one 3, along with small amounts of the 16β-methyl and 16,16-dimethyl derivatives 4 and 5, respectively.

C-1 Hydroxylation

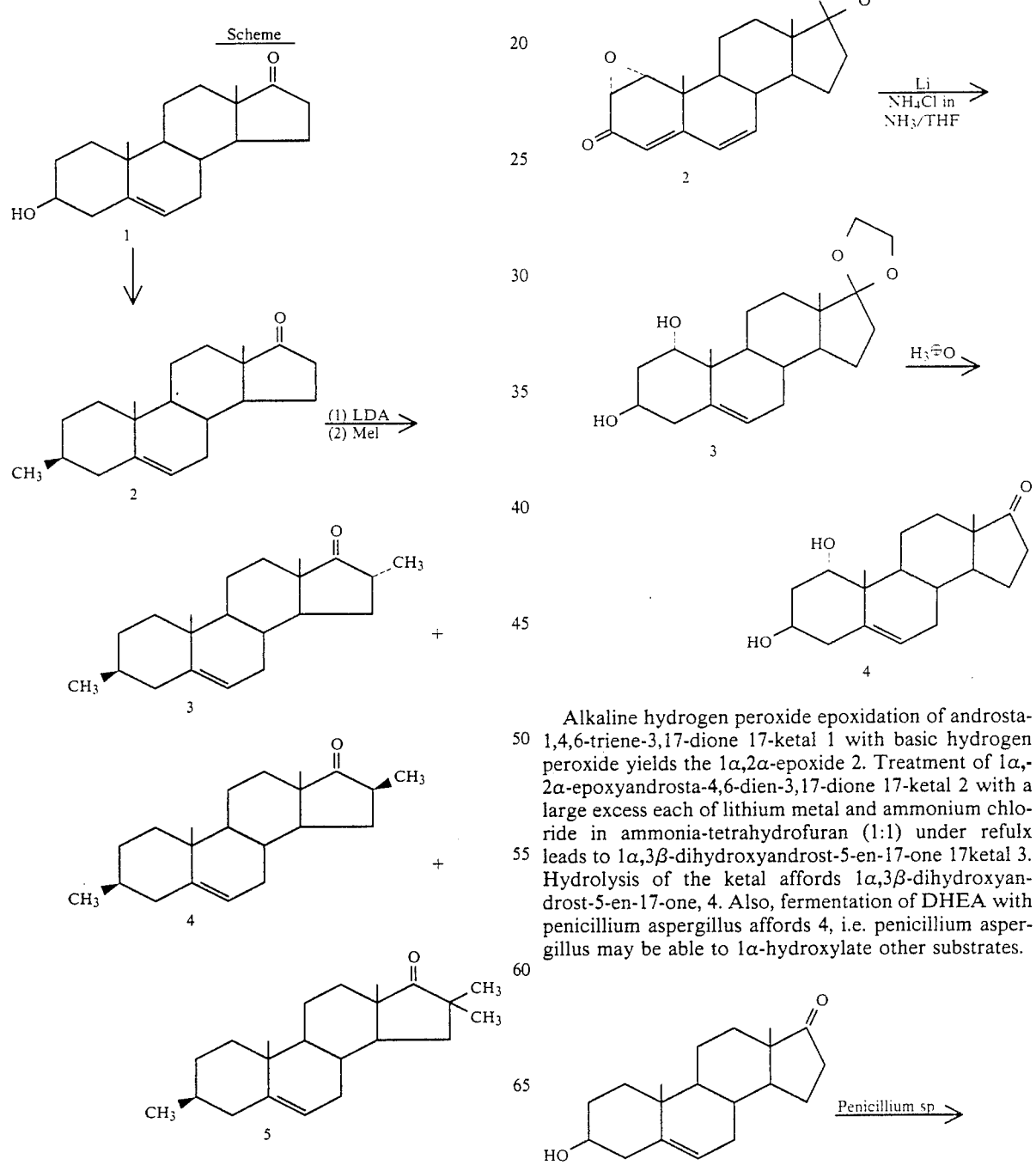

Alkaline hydrogen peroxide epoxidation of androsta-1,4,6-triene-3,17-dione 17-ketal 1 with basic hydrogen peroxide yields the 1α,2α-epoxide 2. Treatment of 1α,2α-epoxyandrosta-4,6-dien-3,17-dione 17-ketal 2 with a large excess each of lithium metal and ammonium chloride in ammonia-tetrahydrofuran (1:1) under refulx leads to 1α,3β-dihydroxyandrost-5-en-17-one 17ketal 3. Hydrolysis of the ketal affords 1α,3β-dihydroxyandrost-5-en-17-one, 4. Also, fermentation of DHEA with penicillium aspergillus affords 4, i.e. penicillium aspergillus may be able to 1α-hydroxylate other substrates.

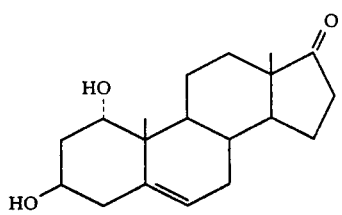

Dodson, R. M., Goldkamp, A. M., and Muir, R. D., *JACS*, 1957, 79, 3921.

Dodson, R. M., Goldkamp, A. M., and Muir, R. D., *JACS*, 1960, 82, 4026.

Penicillium hydroxylates DHEA at C-1 in the α-position. Therefore, other substrates that look like DHEA should be hydroxylated at C-1 by this enzyme.

C-2 Hydroxylation

2α,3β-dihydroxyandrost-5-en-17-one

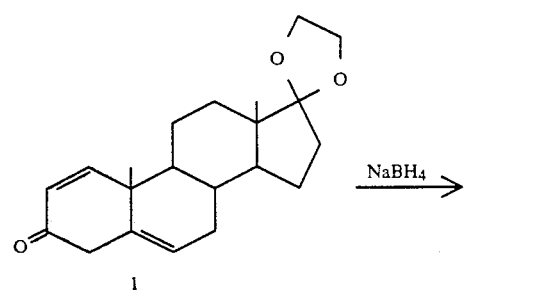

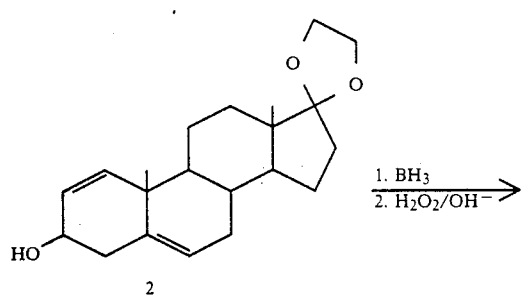

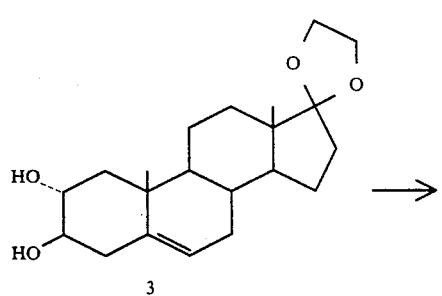

Reduction of androsta-1,5-dien-3,17-dione-17-ketal 1 with sodium borohydride yields 3β-hydroxyandrosta-1,5-diene-17one 17-ketal 2. Hydroxylation of the C-1 doulbe bond by hydroboration followed by oxidation with alkaline hydrogen peroxide affords 2α,3β-dihydroxy-androst-5-en-17-one 17-ketal 3. Deprotection of the C-17 ketone with aqueous acid yields 2α,3β-dihydroxy-androst-5-en-17-one, 4.

Carbon-4 Hydroxylation

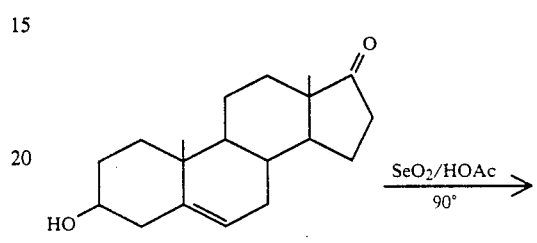

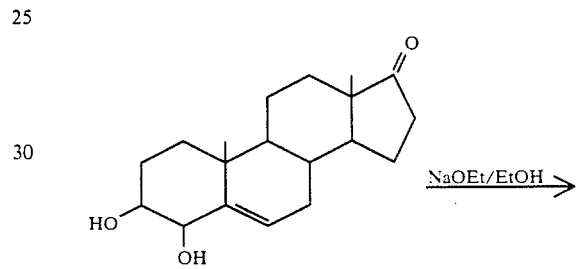

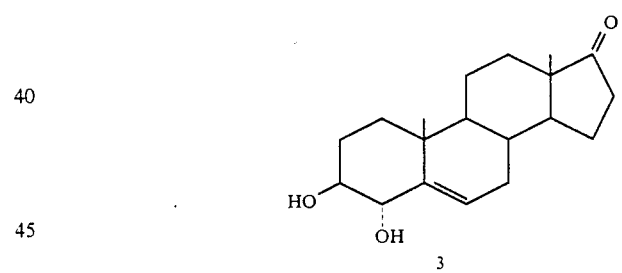

Selenium dioxide oxidation of 3β-hydroxyandrost-5-en-17-one yields 3β,4β-dihydroxyandrost-5-en-17-one 2. The axial C-4 alcohol may be epimerized to the equatorial position by reaction with sodium ethoxide in ethanol to yield 3β,4α-dihydroxyandrost-5-en-17one, 3.

Carbon-7 Hydroxylation

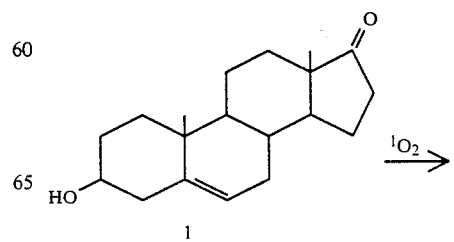

-continued hydroxyandrost-6-en-17one 2. This hydroperoxide undergoes a rearrangement when in chloroform solution to yield 7α-hydroperoxy-3β-hydroxyandrost-5-en-17-one, 3. Treatment of the hydroperoxide with zinc and acetic acid yields 3β,7α-dihydroxy-androst-5-en-17-one, 4.

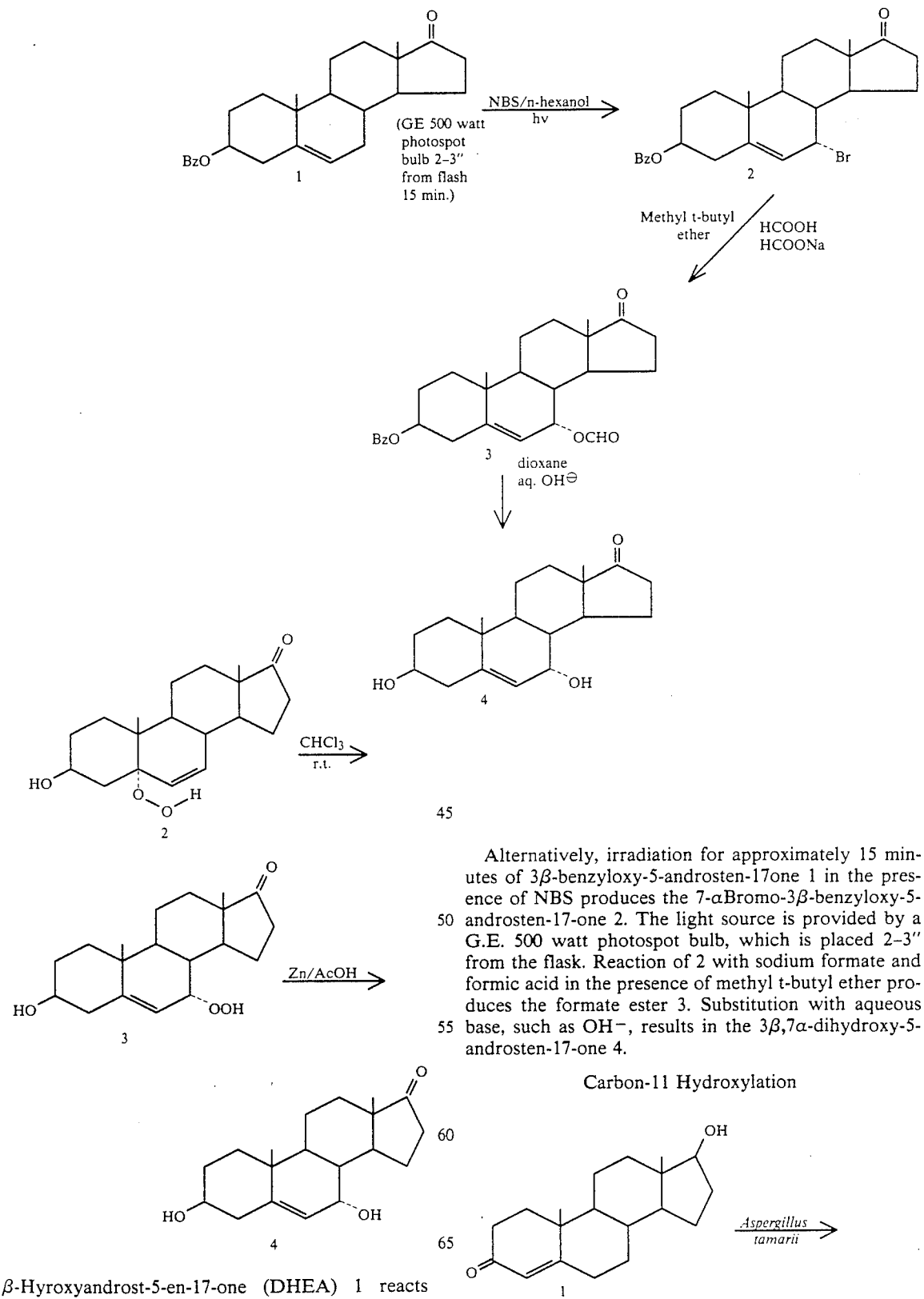

3β-Hyroxyandrost-5-en-17-one (DHEA) 1 reacts with singlet oxygen to yield 5α-hydroperoxy-3β-

Alternatively, irradiation for approximately 15 minutes of 3β-benzyloxy-5-androsten-17one 1 in the presence of NBS produces the 7-αBromo-3β-benzyloxy-5-androsten-17-one 2. The light source is provided by a G.E. 500 watt photospot bulb, which is placed 2-3" from the flask. Reaction of 2 with sodium formate and formic acid in the presence of methyl t-butyl ether produces the formate ester 3. Substitution with aqueous base, such as OH⁻, results in the 3β,7α-dihydroxy-5-androsten-17-one 4.

Carbon-11 Hydroxylation

45
-continued

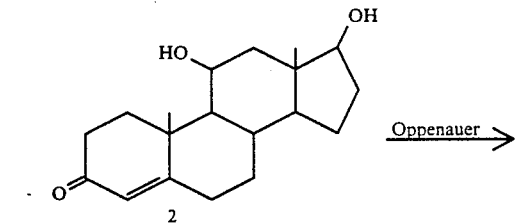

D. R. Brannon, J. Martin, A. C. Ochlschlager, N. N. Durham, and L. H. Zalkow, J. Org. Chem. 1965, 30, 760.

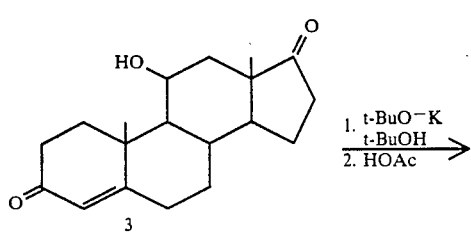

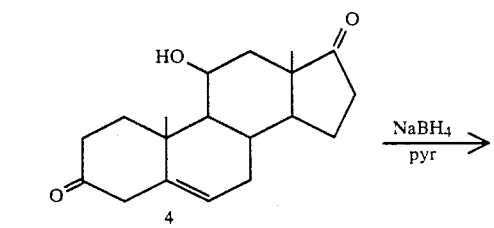

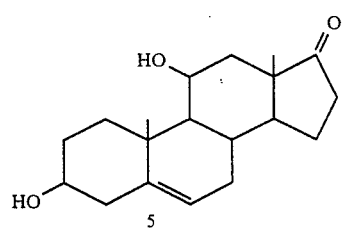

Hydroxylation of testosterone 1 at Carbon-11 using *Aspergillus tamarii* affords 11β,17β-dihydroxyandrost-4-en-3one 2. Oppenauer oxidation of 2 oxidizes the 17β-alcohol in the presence of the hindered 11β-hydroxyl group to yield 11β-hydroxyandrost-4-en-3,17-dione, 3. Migration of the double bond out of conjunction by treatment with potassium t-butoxide followed by protonation with acetic acid yields 11β-hydroxyandrost-5-en-3, 17-dione 4. Selective reduction of 4 yields 3β,11β-dihydroxyandrost-5-en-17-one, 5.

Hydroxylation at Carbon-16

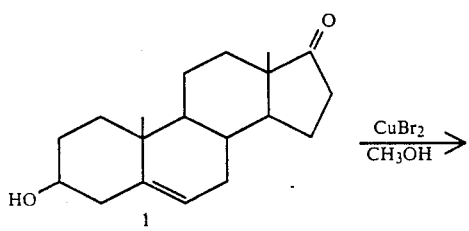

46
-continued

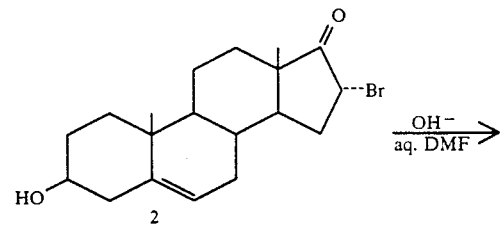

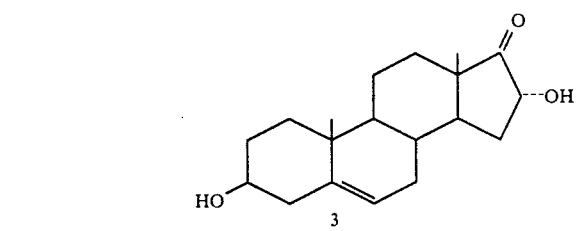

Bromination of DHEA (1) with cupric bromide yields 16α-bromo-DHEA, 2. Treatment of the bromo ketone 2 with sodium hydroxide in aqueous dimethylformamide gave 3β,16α-dihydroxyandrost-5-en-17-one, 3. See M. Numazawa, M. Nagaoka, Y. Osawa, J. Org. Chem. 1982, 47, 4024.

Halogenation

Using techniques known in the art, halogens may be added to the ring. It is preferred that the halogenation step be performed after the ring expansion and after alkylation, hydroxylation or alkoxylation.

The following reactions are meant to be illustrative of the procedures for the halogenation at various positions on the steroidal moiety, and are not meant to be limited to the specific compounds described below. In the reactions described hereinbelow, it is assumed that there is a hydroxy group or the steroidal ring and it is protected using protecting groups known in the art. Obviously, if no hydroxy group is present, then the addition and removal of protecting group need not be performed.

Halogenation at Carbon-1

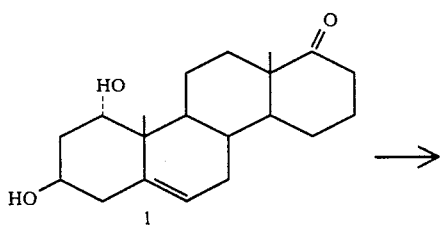

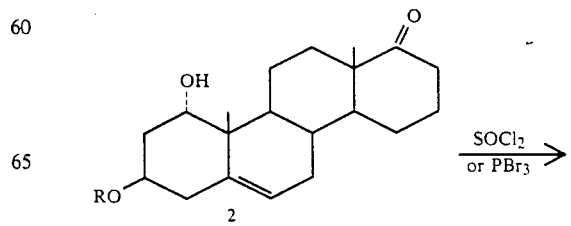

Halogenation at Carbon-3

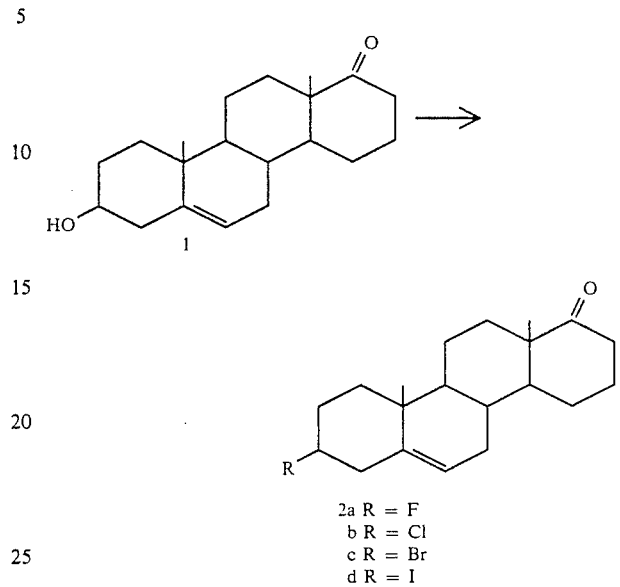

2a R = F
b R = Cl
c R = Br
d R = I

Reaction of 3β-hydroxyhomoandrost-5-en-17a-one 1 with diethyl (2-chloro-1,1,2-trifluoroethyl) amine yields 3β-fluorohomoandrost-5-en-17-one 1. Reaction of 1 with thionyl chloride yields 3β-chlorohomoandrost-5-en-18-one, 2b. Reaction of 1 with phosphorus tribromide yields 3β-bromohomoandrost-5-en-17a-one, 2c. Reaction of 1 with catechol phosphochloridate followed by iodine yields 3β-iodohomoandrost-5-en-17a-one 2d.

Halogenation at Carbon-4

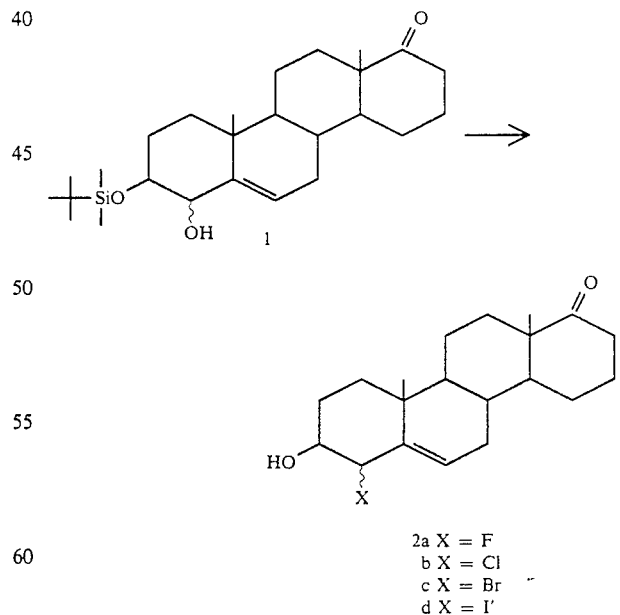

2a X = F
b X = Cl
c X = Br
d X = I'

With the 3β-hydroxyl group protected as its t-butyl-dimethylsilyl ether the C-4 hydroxyl may be chlorinated using thionyl chloride. Treatment with fluoride ion cleaves the silyl ether to yield 4{chloro-3β-hydroxyhomoandrost-5-en-17a-one, 2b. Reaction of 3,4-dihy-

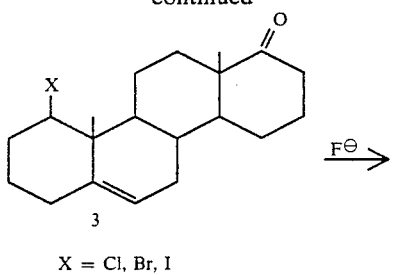

X = Cl, Br, I

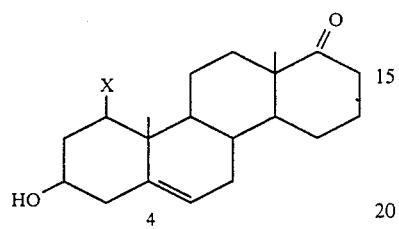

Selective protection of the Carbon-3 hydroxyl in the presence of the 1α-hydroxyl group should yield 2. For example, 1α,3β-dihydroxyhomoandrost-5-en-17a-one 1 reacts with t-butyl-dimethyl silyl chloride in the presence of imidazole using dimethylformamide as a solvent to yield 1α,3β-dihydroxyhomoandrost-5-en-17a-one 3t-butyldimethylsilyl ether, 2. Reaction of 2 with thionyl chloride, or phosphorous tribromide or catechol phosphochloridate followed by iodine yields the corresponding 1β-chloro, bromo or iodo derivatives 3. Reaction of 3 (R=Cl, Br, I) with tetrabutyl ammonium fluoride yields 1β-halo-3β-hydroxyhomoandrost 5-en-17-one, 4 (X=Cl, Br or I). The fluoride (4, X=F) may be synthesized via a similar route using an ester as the protecting group at C-3 and reacting the 1α-hydroxyl group with diethyl (2-chloro-1,1,2-trifluoroethyl)amine. Hydrolysis should yield 1β-fluoro-3β-hydroxyhomoandrost-5-ene-18one, 4, X=F.

Halogenation at Carbon-2

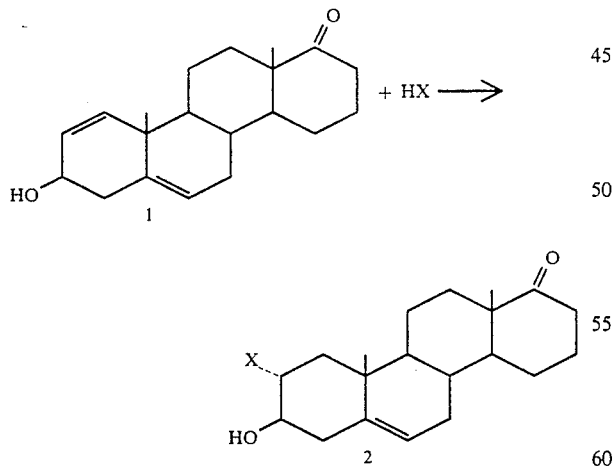

Addition of HX across the C-1 double bond in 3β-hydroxyhomoandrosta-1,5-diene-17a-one, 1, yields a mixture of the C-1 and C-2 halogenated steroids. Separation affords 2-halo-3β-hydroxyhomoandrost-5-en-17a-one (2, X=F, Cl, Br, I).

If desired, the 3-OH group can be converted to the corresponding 3-H, 3-alkyl, 3-halo or 3-alkoxy derivatives by using the appropriate procedures described herein.

droxyhomoandrost-5-en-17a-one 3-t-butyldimethylsilyl ether 1 with 0-phenylene phosphochloridite, followed by displacement with bromide ion and cleavage of the silyl ether with fluoride ion yields 4{bromo-3β-hydroxyhomoandrost-5-en-17a-one, 2c. Reaction of 1 with catechol phosphochloridate, followed by iodine and cleavage of the silyl ether with fluoride yields 4{iodo-3β-hydroxyhomoandrost-5-en-17a-one, 2d. Fluorination of 3β,4{dihydroxyhomoandrost-5-en-17a-one 3-acetate with diethyl (2-chloro-1,1,2-trifluoroethyl)amine followed by hydrolysis of the ester yields 4{fluoro-3β-hydroxyhomoandrost-5-en-17a-one, 2a.

If desired, the 3-hydroxy group can be converted to the corresponding 3-H, 3-alkyl, 3-alkoxy or 3-halo derivative by using the appropriate procedures described herein.

Halogenation at Carbon-6

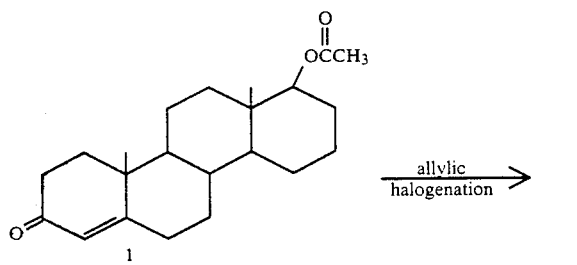

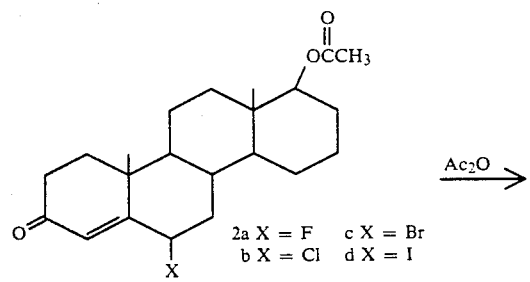

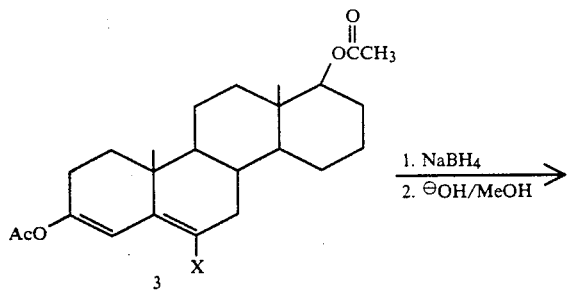

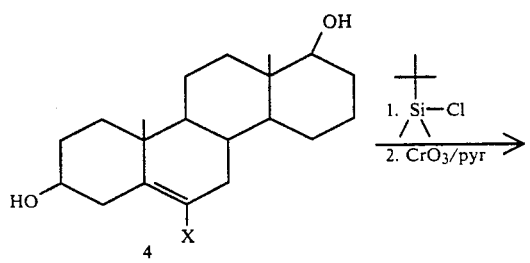

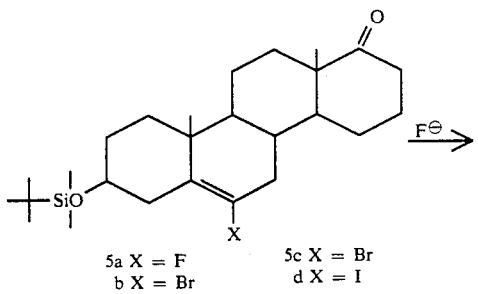

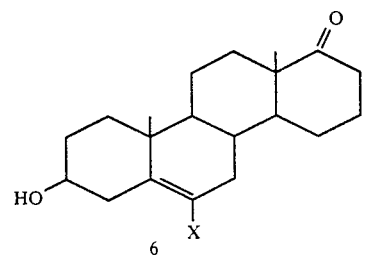

Allylic bromination of 17aβ-hydroxyhomoandrost-4-en-3-one 17a-acetate 1 using N-bromosuccinimide together with a radical initiator such as light or benzoyl peroxides or aliphatic azo compounds [RR'C(CN)—N=N—C(CN)RR'] e.g. azobisisobutyronitrile yields.6β-bromo-17aβ-hydroxyhomoandrost-4-en-3-one 17a-acetate, 2. Allylic chlorination of 1 using sulfuryl chloride together with a radical initiator such as light or benzoyl peroxide or aliphatic azo compounds yields 6β-chloro-17aβ-hydroxyhomoandrost-4-en-3-one 17a-acetate, 2c. Allylic iodination of 1 using mercuric iodide and light yields 6β-iodo-17aβ-hydroxyhomoandrost-4-en-3-one-17a-acetate, 2d. Acetylation of 2 with acetic anhydride and p-toluene sulfonic acid in toluene yields 6-halo-3,17aβ-dihydroxyhomoandrosta-3,5-diene 3,17a-diacetate 3. Sodium borohydride reduction of 3 followed by basic hydrolysis of the C-17a acetate yields 6-halohomoandrost-5-en-3β,17aβ-diol, 4. Selective protection of the C-3 hydroxyl group as its t-butyldimethylsilyl ether followed by chromium trioxide oxidation of the C-17a-hydroxyl group yields 6-halo-3β-hydroxyhomoandrost-5-en-17a-one 3-t-butyl-dimethyl-silyl ether 5. Treatment of 5 with fluoride ion yields 6-halo-3β-hydroxyhomoandrost-5-en-17a-one, 6. The C-6 fluoro analogue may be synthesized from the C-6 bromo diacetate, 3c, by treatment with silver fluoride. Following the above sequence, reaction of 6-fluoro-3,17aβ-dihydroxy-homoandrosta-3,5-diene-3,17a-diacetate, 3a with sodium borohydride yields, 6-fluoro-3β-hydroxyhomoandrost-5en-17a-one, 6a.

If desired, the 3-OH group can be converted to the corresponding 3-H., 3-alkyl, 3-halo or 3-alkoxy derivatives by using the appropriate procedures described herein.

Halogenation at Carbon-7

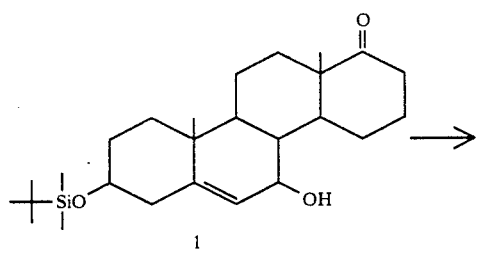

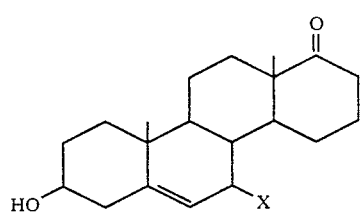

2a X = F
b X = Cl
c X = Br
d X = I

Reaction of 3β,7-dihydroxyhomoandrost-5-en-17a-one-3-t-butyldimethylsilyl ether 1 with thionyl chloride yields the C-7 chloro-steroid. Deprotection of the 3β-hydroxyl group affords 7-chloro-3β-hydroxyhomoandrost-5-en-17a-one, 2b. Reaction of 1 with catechol phosphochloridate followed by displacement with bromide ion and deprotection yields 7-bromo-3β-hydroxyhomoandrost-5-en-17a-one, 2c. Similarly reaction of 1 with catechol phosphochloridate followed by displacement with iodine and deprotection yields 7-iodo-3β-hydroxyhomoandrost-5-en-17a-one, 2d. Fluorination of 3β,7-dihydroxyhomoandrost-5-en-16-a-one 3-acetate with diethyl (2-chloro-1,1,2-trifluoroethyl) amine followed by hydrolysis of the ester yields 7-fluoro-3β-hydroxyhomoandrost-5-en-17a-one, 2a.

If desired, the 3-OH group can be converted to the corresponding 3-H, 3-alkyl, 3-halo or 3-alkoxy derivatives by using the appropriate procedures described herein.

Halogenation at Carbon-9

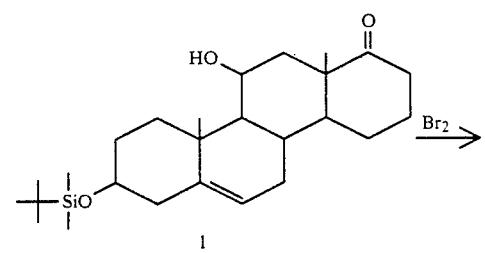

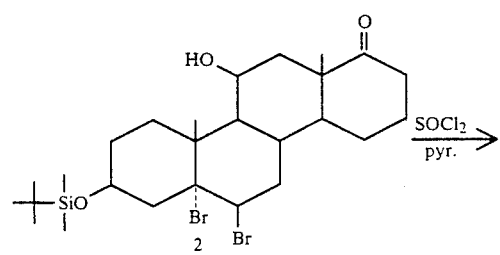

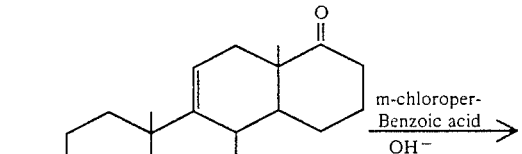

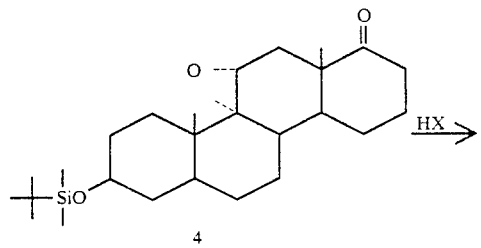

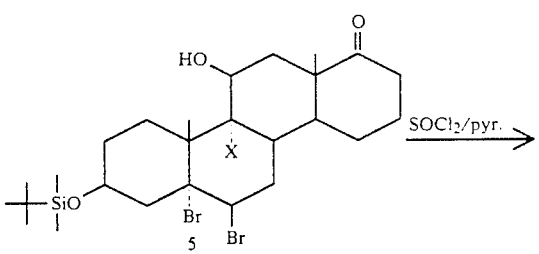

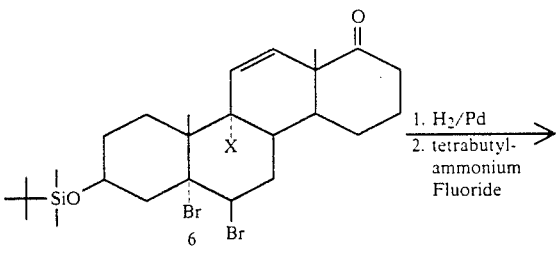

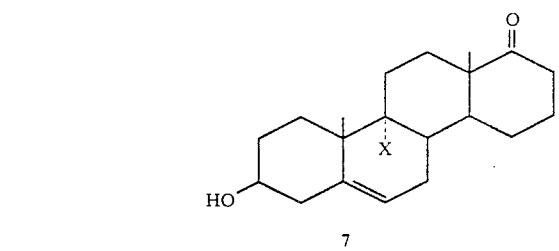

Bromination of 3β,11α11α-dihydroxyhomoandrost-5-en-17a-one 3-t-butyldimethylsilyl ether 1 yields the dibromide 2. Reaction of 2 with thionyl chloride produces the unsaturated compound, 3β-hydroxy-5,6-dibromo-9(11)-homoandrosten-17a-one-3-t-butyl-dimethylsilyl ether 3. 3 is epoxidized with perbenzoic acid forming 4. Reaction of 4 with hydrohalic acid, such as HCl, HBr, forms the 9α-halo derivative 5. Dehydration of 5 with thionyl chloride produces the unsaturated compound, the 3β-hydroxy-5,6-dibromo-11-homoandrosten-17a-one-3-t-butyl-dimethylsilyl ether 6. Catalytic hydrogenation of 6 followed by removal of the protecting group forms the 3-βhydroxy-9-α-halo-5-homoandrosten-17a-one.

If desired, the 3-OH group can be converted to the corresponding 3-H, 3-alkyl, 3-halo or 3-alkoxy derivatives by using the appropriate procedures described herein.

Halogenation at Carbon-11

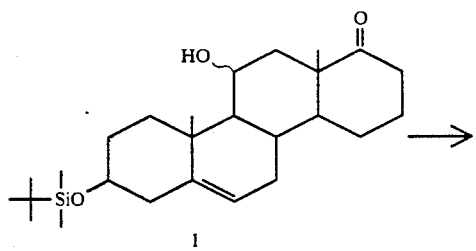

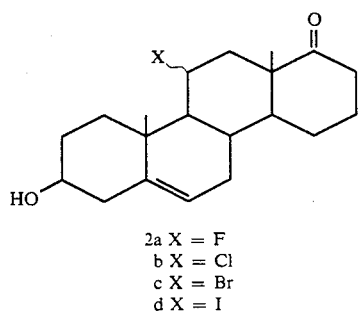

2a X = F
b X = Cl
c X = Br
d X = I

Reaction of 3β,11α-dihydroxyhomoandrost-5-en-17a-one 3-t-butyldimethylsilyl ether 1 with OPPC followed by chloride yields the C-11 chloro steroid. Deprotection of the 3β-hydroxyl groups affords 11{-chloro-3β-hydroxyhomoandrost-5-en-17a-one, 2b. Reaction of 1 with OPPC followed by displacement with bromide ion and deprotection yields 11{-bromo-3β-hydroxy-homoandrost-5-en-17a-one, 2c. Similarly reaction of 1 with OPPC followed by displacement iodine and deprotection yields 11{-iodo-3β,hydroxyhomoandrost-5-en-17a-one 2d. Fluorination of 3β,11α-dihydroxy-homoandrost-5-en-17a-one 3-acetate with diethyl (2-chloro-1,1,2-trifluoroethyl)amine followed by hydrolysis of the ester yields 11{-fluoro-3β-hydroxyhomoandrost-5-en-17-one, 2a.

If desired, the 3-OH group can be converted to the correponding 3-H, 3-alkyl, 3-halo or 3-alkoxy derivatives by using the appropriate procedures described herein.

Similarly, the alkyl derivatives of 17 halo-5-homoandrosten-17a-one derivatives can be prepared using synthetic pathways known in the art. For example, using the procedure of the alkylation method described supra the 17-halo derivatives produced by the procedures described hereinabove is alkylated to produce the alkyl derivative of 17-halo-5-homoandrosten-17-ones. As an example, 17 halo derivatives can be alkylated in the 3-position using the techniques described hereinabove to form 3 alkyl-17-halo-5-homoandrosten-17a-ones. Alternatively, the alkyl derivatives can be prepared using the methods described supra and then halogenated by the methods described hereinabove. For example, halogenation of 3-alkyl-5-homoandrosten-17a-one by the method described hereinabove would afford the corresponding 3-alkyl-? 7-halo-5-homoandrosten-17a-ones.

Another method for the preparation of the 11βsteroids is as follows:

The corresponding 11α-hydroxy derivative can be reacted with N-(2-chloro-1,1,2-trifluoroethyl)diethylamine to give the 11β-fluoro derivative (2a) or in the presence of lithium chloride or lithium bromide to give the 11β-chloro (2c) and 11β-bromo derivative (2c) respectively, according to the procedure of Bailey, et al. in Chemical Communications, 106-107, (1970).

The following procedures are illustrative for the preparation of the homoandrostane compounds of the present invention:

Catalytic hydrogenation of 3β-substituted homoandrost-5-enes yields almost exclusively 3β-substituted 5α-homoandrostanes (for references see J. R. Lewis and C. W. Shoppee, *J. Chem. Soc.* 1955, 1365). Therefore all the syntheses of the substituted homoandrost-5-enes described above can be used for the syntheses of the substituted 5α-androstanes.

An example of catalytic hydrogenation for the synthesis of 5α-homoandrostanes from homoandrost-5enes is the synthesis of 3β-methyl-5α-homoandrostan-17a-one 2 from 3β-methylhomoandrost-5-en-17a- one 1. 3β-Methylhomoandrost-5-en-17a-one -1 (400 mg), prepared according to the procedures described herein previously was dissolved in glacial acetic acid (80 ml). Palladium on carbon (10%, 100 mg) was added and the solution maintained under an atmosphere of hydrogen. When hydrogen uptake ceased, the solution was filtered through celite and evaporated to give a solid which was recrystallized from methanol to yield 3β-methyl-5α-homoandrostan-17a-one, 2.

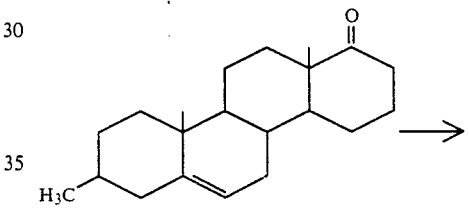

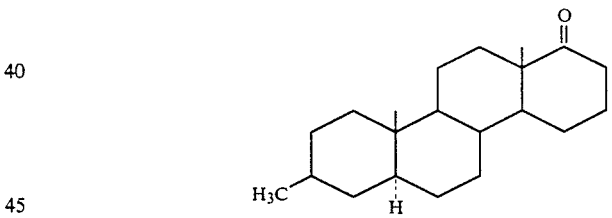

The following examples further illustrate the invention:

EXAMPLE I

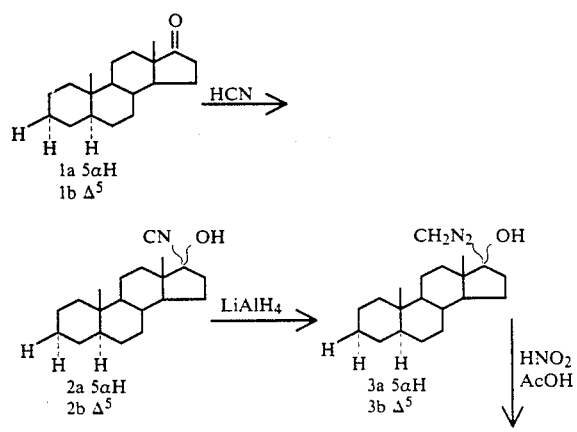

-continued

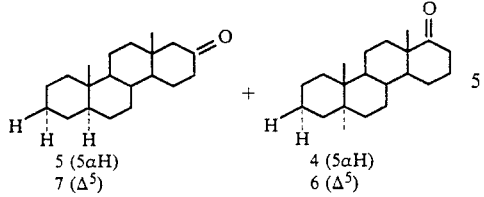

5α-D-Homoandrostan-17a-one(4)

Tiffeneu Demyanov ring enlargement of the 17-one 1 by the method of Goldberg and Monnier (Helv. Chim. Acta 23, 376 (1940)) as modified by Kirk and wilson (J. Chem. Soc., p. 64, 1970) is carried out via the cyanohydrin mixture (2) and the 17{-hydroxy-17{aminomethyl (3). Nitrosation of 3 affords the D-homo steroid 4 as the major product and the 17-keto-D-homosteroid 5 as a minor product.

Similar reaction of 5-androsten-17-one gives the corresponding olefins 6 and 7.

EXAMPLE II

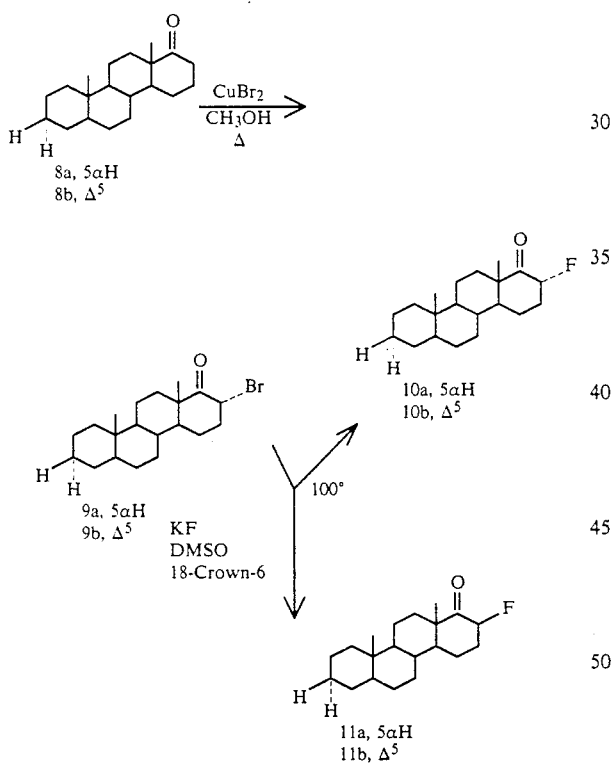

17α-and17β-Fluoro-5α-D-Homoandrosten-17-ones(10a and 11a) and 17α-and 17β-Fluoro-5-D-homoandrosten-17a-ones (10b and 11b)

Refluxing the D-homo-17α-ones (8a and 8b) with methanolic cupric bromide furnishes the 17α-bromo-17a-ones 9a and 9b as the principal products. Reaction of the α-bromo ketones with potassium fluoride/18-Crown-6/Dimethylsulfoxide at 100° for 2-4 hours affords both possible 17-fluorides (10a, b and 11a, b). Separation of the epimers is carried out by preparative HPLC.

EXAMPLE III

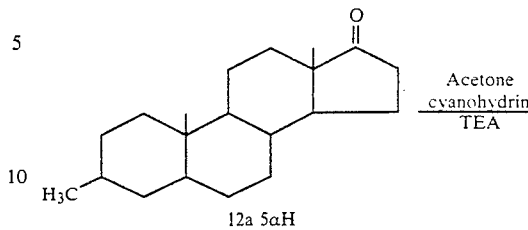

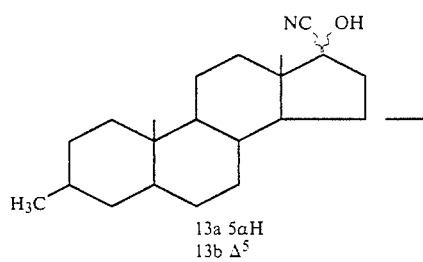

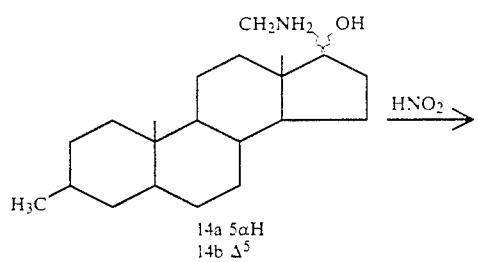

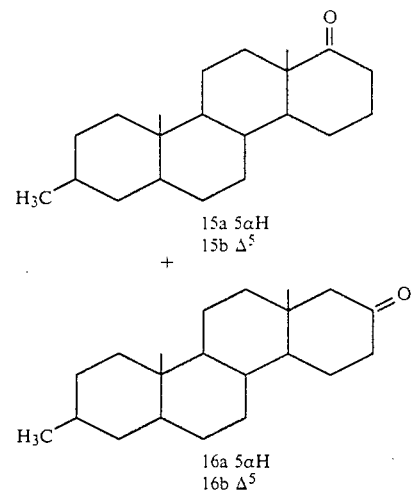

3β-methyl-5-homoandrostene-17a-one-(15b)
3B-methyl-5α-homoandrostan-17a-one (15a)

3β-methyl-5-homoandrostene-17-one-(16b)
3B-methyl-5α-homoandrostan-17a-one (16a)

The 3β-methyl-17-one (12a or 12b) is dissolved in acetone and reacted with cyanohydrin in the presence of triethylamine followed by reduction by lithium aluminum hydride according to the procedure of Goldberg and Monnier (Helv. Chim. Acta, 23, 376) (1940) as modified by Kirk and Wilson (J. Chem. Soc., p. 64, (1970), forming the corresponding 17{hydroxy-17{aminomethyl derivatives (14a and 14b). Nitrosation of 14a affords the D homosteroids (15a) as the major product and the 17 keto-D-homosteroid 16a as the minor product.

Similarly, nitrosation of 14b affords the D homosteroid (15b) as the major product and the 17-keto-D-homosteroid (16b) as the minor product.

EXAMPLE IV

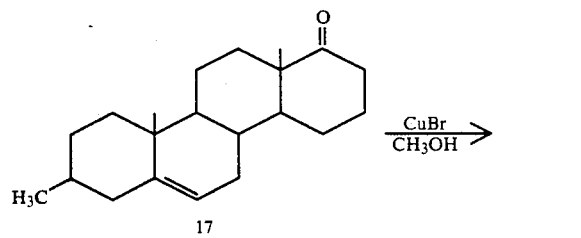

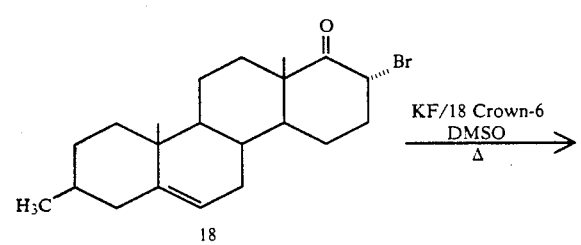

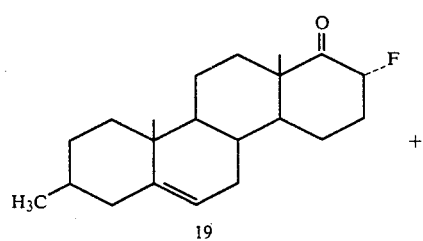

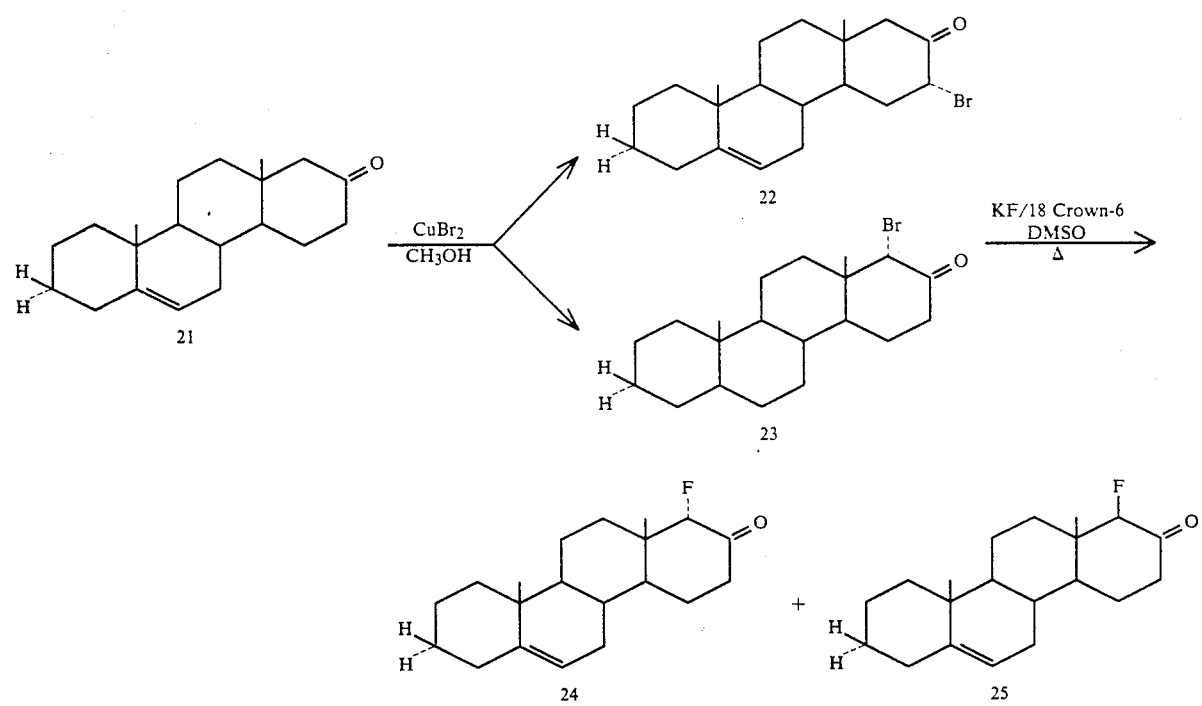

17α and 17β-Fluoro-5-D-Homoandrosten-17a-one (19 and 20)

Using the procedure described in Example II hereinabove, the above products were prepared. More particularly, refluxing the 3β-methyl-5-D-homoandrosten-17a-one (17) with methanolic cupric bromide furnishes the 3β-methyl-17αbromo-17a-one (18) as the principal product. Reaction of 18 with potassium fluoride/18-Crown-6/Dimethyl sulfoxide at 100° for 2-4 hours affords both possible 17-fluorides (19 and 20). Separation of the epimers is carried out by preparative HPLC.

EXAMPLE V

17aα and 17aβ-Fluoro-5-D-Homoandrosten-17-one (24 and 25)

Refluxing 5D-homoandrosten-17-one (21) with methanolic cupric bromide furnishes the 17aα-Bromo-5-Homoandrosten-17-one (23) and 16α-bromo-5-homoandrosten-17-one (22). The isomers are separated out by preparative HPLC. 23 is then reacted with potassium fluoride/18-Crown-6/Dimethyl sulfoxide at approximately 100° for 2-4 hours to afford both possible fluorides (24 and 25). Separation of the epimers is carried out by preparative HPLC.

EXAMPLE VI

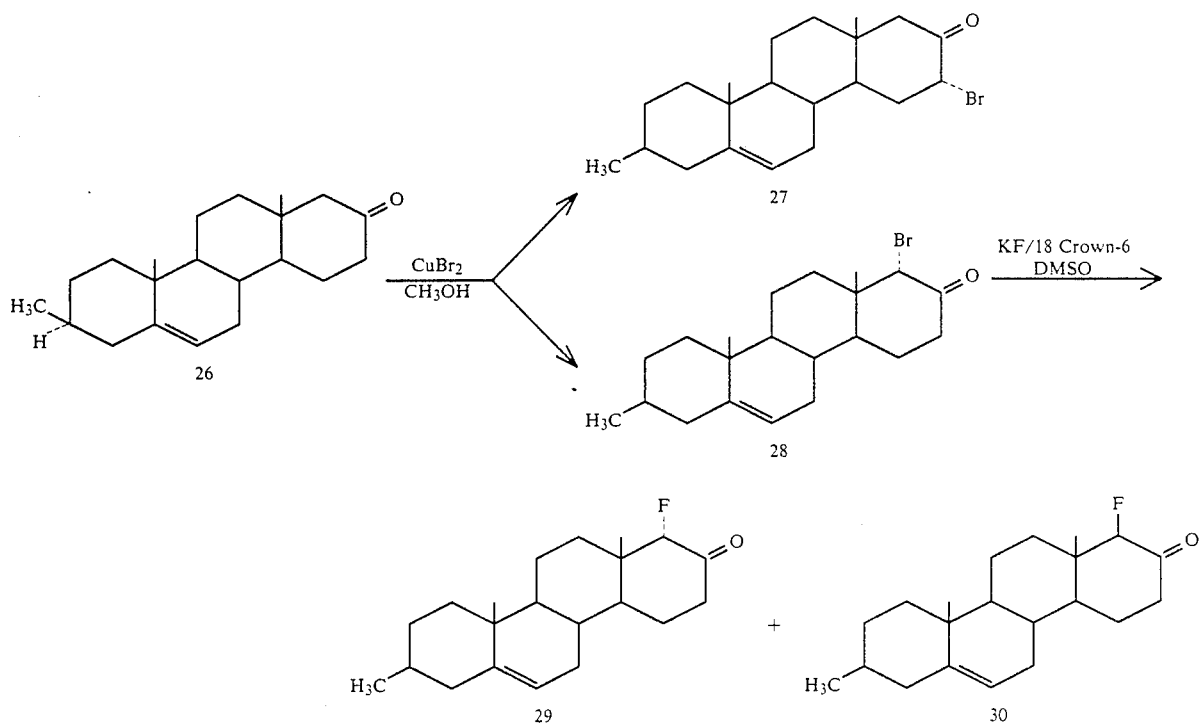

17aα and
17aβ-Fluoro-3β-methyl-5-D-homoandrosten-17-one (29 and 30)

Refluxing 3β-methyl-5-D-homoandrosten-17-one (26) with methanolic cupric bromide furnishes the 17aα-Bromo-5-homoandrosten-17-one (28) and 16α-bromo-5-homoandrosten-17-one (27), which are separated by preparative HPLC. 28 is then reacted with potassium fluoride/18-Crown-6/Dimethyl sulfoxide at approximately 100° C. for 2–4 hours to afford both possible fluorides (29 and 30). Separation of the epimers is carried out by preparative HPLC.

EXAMPLE VII

3β-methyl-5α-D-homoandrostan-17-one

To a solution of 3β-methyl-5-D-homoandrostan-17a-one (produced in Example III) in 500 ml of ethanol is added 5% pd on C and the mixture is exposed to a hydrogen atomosphere while stirring. The catalyst is filtered off and the above-identified product is isolated.

EXAMPLE VIII

3β-methyl-5α-D-homoandrostan-17-one

Using 3β-methyl-5D-homoandrosten-17-one which is produced in Example III as the starting material and following the procedure described in Example VII, the above product is formed.

EXAMPLE IX

3β-methyl-17α-fluoro-5α-D-homoandrostan-17a-one

3β-methyl-17β-fluoro-5α-D-homoandrostan-17a-one

Using 3β-methyl-17α-fluoro-5D-homoandrostene-17a-one, and 5βmethyl-17β-fluoro-5D-homoadnrostene-17one which are produced respectively in Example IV, as the starting material and following the procedure outlined in Example VII, the above-products are formed.

Alternatively, the above products can be formed by substituting 3β-methyl-5α-D-homoandrostan-17a-one for 3β-methyl-5-D-homoandrostene-17-a-one and following the procedure of Example IV.

EXAMPLE X

17a α-Fluoro-5α-D-homoandrostan-17-one

17a β-Fluoro-5α-D-homoandrostan-17-one

Using 17a α-fluoro-5-D-homoandrostan-17-one, produced in Example V, as the starting material and following the procedure of Example VII, 17a α-Fluoro-5α-D-homoandrostan-17-one is formed.

Similarly, by using 17aβ-fluoro-5-D-homoandrosten-17-one, produces in Example V as the starting material and following the procedure of Example VII, the 17aβ-fluoro-5α-D-homoandrostan-17-one is produced.

Alternatively, the above products can be prepared by following the procedure of Example v and using 5α-D-homoandrostan-17-one as the starting material.

EXAMPLE XI

17aα-fluoro-3β-methyl-5α-D-homoandrostan-17-one

Using 17aβ-fluoro-3β-methyl-5-D-homoandrosten-17-one, produced in Example VI, as the starting material and following the procedure outlined in Example VII, the above-product is formed.

Using 17a β-fluoro-3β-methyl-5-D-homoandrosten-17-one, produced in Example VI, as the starting material and following the procedure outlined in Example VII, the 17aβ-fluro-3β-methyl-5α-D-homoandrosten-17-one is formed.

Alternatively, the above products can be prepared by following the procedure of Example VI and using 3β-methyl-5-D-homoandrosten-17 one as the starting material.

Preparation of 17aα-methyl-5-D-homoandrosten-17-one (8), 17aα-methyl-5α-D-homoandrostan-17-one (9), 17α-methyl-5-D-homoandrosten-17a-one (7), and 17α-methyl-5-D-homo androstan-17a-one.
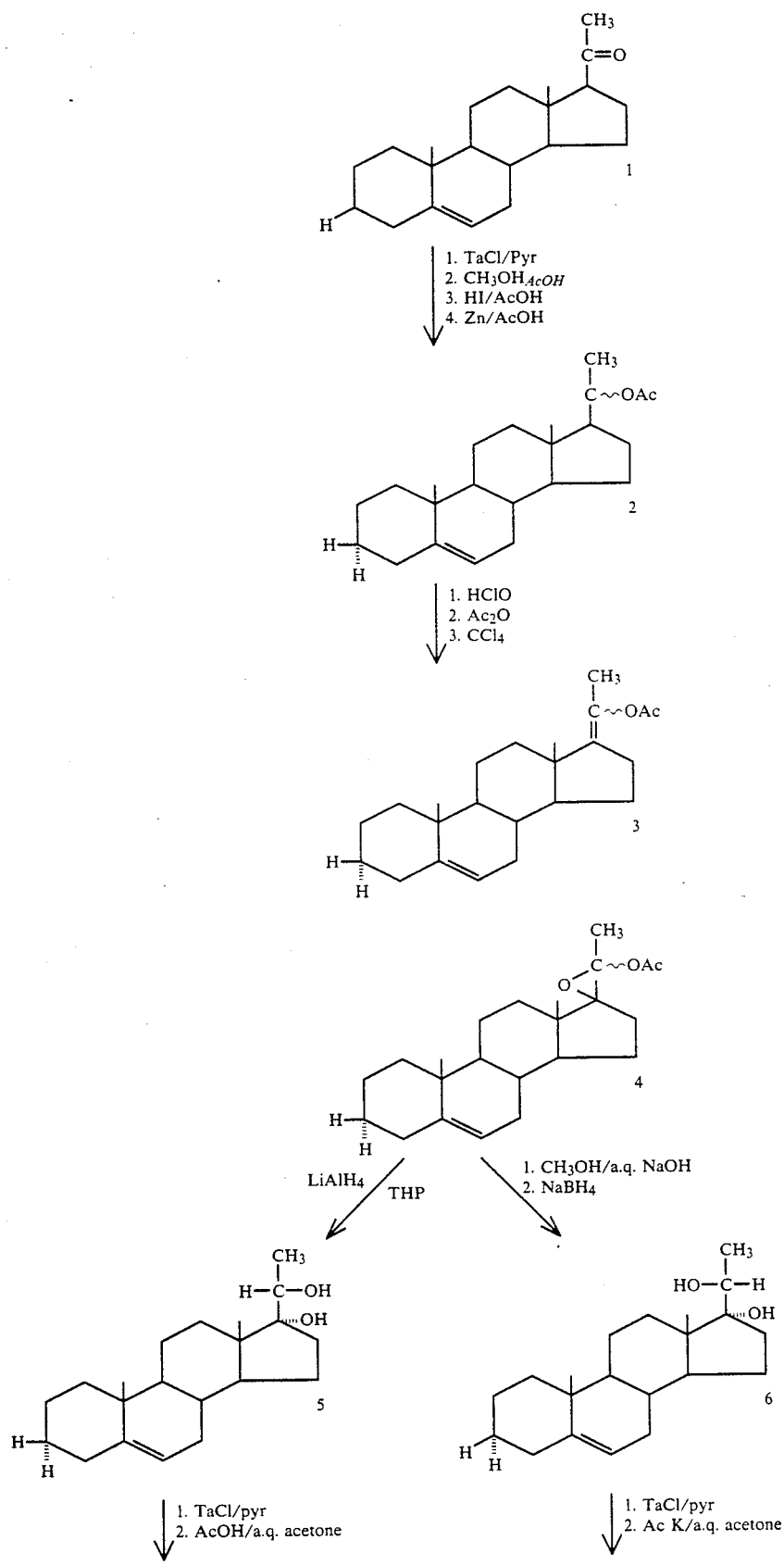

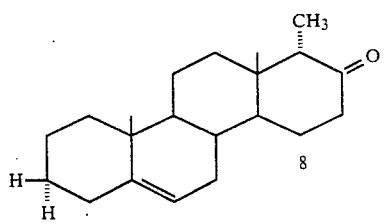
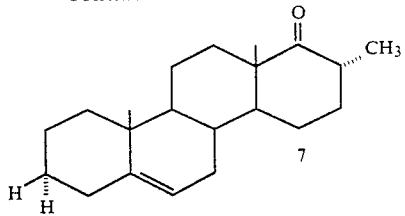

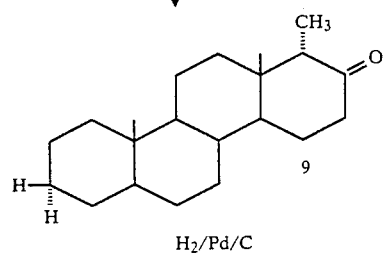
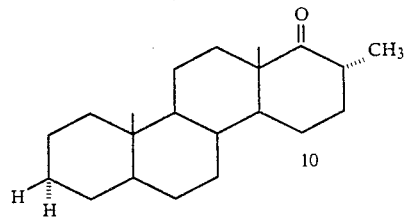

Preparation of 5-pregnen-20-one(2) was accomplished in 4 steps from pregnenolone (1) utilizing the 6α-methoxy-i-steroid as key intermediate. Enol acetylation of 2 by the procedure of Barton et al. in Journal Chem. Soc.. of London 1747 (1954) supplies 3. Treatment of 3 in benzene with m-chloroper benzoic acid gives the 17, 20 epoxy-20-acetate 4. Reduction of 4 with lithium aluminum hydride gives the 17, 20α-diol 5: sequential identification of 4 followed by sodium borohydride reduction gives the 17, 20α-diol 6. Solvolysis of the respective C-20 tosylates with potassium acetate in aqueous acetone affords the 17aα-methyl-17-one (8) from 5 and the 17α-methyl-17a-one (7) from 6. Catalytic hydrogenation of the D-homosteroids 7 and 8 provides the respective D-homo-5α-androstanes 9 and 10.

Similarly, using the above procedure, and the appropriate starting materials, the following compounds can also be prepared.

3β, 17aα-dimethyl-5-D-homoardrosten-17-one
3β, 17aα-dimethyl-5 -D-homoandrostan-17-one
3β, 17α-dimethyl-5-D-homoandrosten-17a-one
3β, 17α-dimethyl-5α-D-homoandrostan-17a-one Researchers have found that there is a good correlation between compound's efficacy in the inhibition of mammalian glucose 6-phosphate dehydrogehase (G6 PDH inhibition) and its of cancer prophylatic activity. The assay for testing the inhibition of purified bovine adrenal G6PDH is described by Oertel, G. W. and Rebebun, F., in *Biochem. Biophys. Acta*, 184, 459–460 (1969).

The results of representative compounds are shown below:

| Compound | Conc. | Percent G6PDH inhibition |
| --- | --- | --- |
| 17-keto-D-homo DHEA | $10^{-5}M$ | 24, 29 |
| 3 β-hydroxy-D-homo-5-androsten-17a-one | $10^{-5}M$ | 60, 58 |
| | $10^{-6}M$ | 16, 15 |

Compounds of the present invention are effective cancer preventive agents. It has been shown that compounds of this sort are effective inhibitors of G6PDH dehydrogenase.

Compounds of the present invention are also effective anti-obesity agents. In fact, the compounds wherein the B ring of the steroid contains a double bond in the 5,6 position are more effective anti-obesity agents than the saturated counterpart, which has some effectiveness in the obesity test. On the other hand, the saturated counterparts are more effective in the anti-cancer tests than are the unsaturated steroids containing a double bond in the 5,6 position, which by the way also exhibit anti-cancer activity. Therefore, the anti-cancer effect and the anti-obesity effect can be separated out. As a result, the physician can proscribe drugs wherein he can emphasize one effect relative to the other.

The compounds of the present invention are also effective anti-hyperglycemic agents, anti-hypercholesterolemic agents and anti-aging agents. Moreover, the compounds of the present invention are effective anti-auto-immune agents, and are effective in the prophylaxis and treatment of auto-immune diseases such as lupus erythematosis and Coomb's positive hemolytic anemia.

The compounds of the present invention do not possess the side effects that are exhibited by other steroids. Unlike other steroids such as DHEA, the compounds of the present invention do not exhibit an estrogen effect. Furthermore, the compounds of the present invention do not exhibit liver enlargement, which is prevalent with other steroids, such as DHEA.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. For parental administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages, substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with those other therapeutic agents.

When given orally, the therapeutic doses of the compounds of the present invention are generally in the range of from about 4 to about 450 mg/kg/day depending upon the particular mammalian host and the particular effect desired, e.g. cancer preventive, anti-obesity, anti-diabetes, etc. When given parenterally, the compounds are administered generally in dosages of, for example, 0.5 to about 15 mg/kg/day, also depending upon the host and effect desired.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils, The proper fluidity can be maintained, for example, by the use of a coating such as lecithin, by the maintenance of the required particle size in the case of dispersion and by the use of surfactants. The prevention of the actIon of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Obviously, other modifications and variations of the present invention are possible in light of the above teachings. It is, therefore, to be understood that changes may be made in the particular embodiments of this invention which are within the full intended scope of the invention as defined by the appended claims.

What is claimed is:

1. A compound of the formula

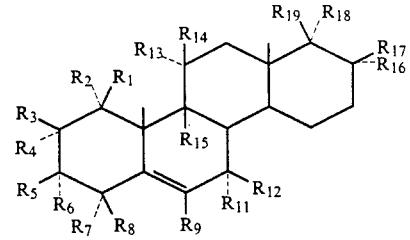

wherein
$R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen hydroxy or lower alkoxy;

$R_5$ and $R_6$ are independently hydrogen, lower alkyl, halogen or lower alkoxy;

$R_9$ is hydrogen, lower alkyl or halogen; and $R_{16}$, $R_{17}$, $R_{18}$ and $R_{19}$ are each independently hydrogen, lower alkyl, hydroxy or halogen; or $R_{16}$ and $R_{17}$ taken together or $R_{18}$ and $R_{19}$ taken together are each independently oxo, with the proviso that said compound contains only one oxo group.

2. The compound according to claim 1 wherein the lower alkyl group and lower alkoxy group contains 1-3 carbon atoms.

3. The compound according to claim 1 wherein lower alkyl is methyl.

4. The compound according to claim 1 wherein halogen is fluorine.

5. The compound according to claim 1 wherein $R_5$ is hydrogen or methyl.

6. The compound according to claim 5 wherein $R_1$, $R_2$, $R_3$, $R_4$, $R_6$, $R_7$, $R_8$, $R_9$, $R_{11}$, $R_{12}$, $R_{13}$, $R_{14}$ and $R_{15}$ are hydrogen.

7. A compound of the formula:

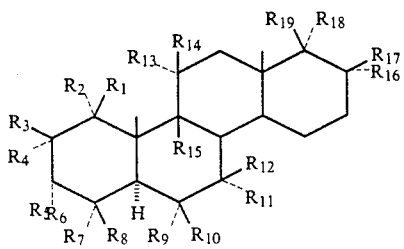

wherein
- $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;
- $R_5$ and $R_6$ are independently hydrogen, lower alkyl or halogen;
- $R_9$ and $R_{10}$ are each independently hydrogen, lower alkyl or halogen;
- $R_{16}$, $R_{17}$, $R_{18}$ and $R_{19}$ are each independently hydrogen, alkyl containing from 2-6 carbon atoms, hydroxy, chloro or fluoro; or
- $R_{16}$ and $R_{17}$ taken together or $R_{18}$ and $R_{19}$ taken together are each independently oxo, with the provisos that said compound contains only one oxo group and that when $R_{18}$ and $R_{19}$ taken together are oxo, and $R_{16}$ $R_{15}$ are hydrogen, then at least one of $R_{16}$ and $R_{17}$ is hydroxy, fluoro or chloro.

8. The compound according to claim 7 wherein the lower alkyl group of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ and lower alkoxy group contain 1-3 carbon atoms.

9. The compound according to claim 7 wherein the lower alkyl of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ is methyl.

10. The compound according to claim 7 wherein halogen is fluorine.

11. The compound according to claim 7 wherein $R_5$ is hydrogen or methyl.

12. The compound according to claim 7 wherein $R_1$, $R_2$, $R_3$, $R_4$, $R_6$, $R_7$, $R_8$, $R_9$, $R_{10}$, $R_{11}$, $R_{12}$, $R_{13}$, $R_{14}$ and $R_{15}$ are hydrogen.

13. A compound of the formula:

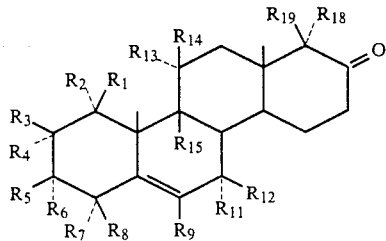

wherein
- $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;
- $R_5$ and $R_6$ are independently hydrogen, lower alkyl, halogen or lower alkoxy;
- $R_9$ is hydrogen, lower alkyl, or halogen; and
- $R_{18}$ and $R_{19}$ are each independently hydrogen, lower alkyl, hydroxy or halogen.

14. The compound according to claim 13 wherein the lower alkyl and lower alkoxy group contain 1-3 carbon atoms.

15. The compound according to claim 13 wherein lower alkyl is methyl.

16. The compound according to claim 13 wherein halogen is fluorine.

17. The compound according to claim 13 wherein $R_5$ is hydrogen or methyl.

18. The compound according to claim 17 wherein $R_1$, $R_2$, $R_3$, $R_4$, $R_6$, $R_7$, $R_8$, $R_9$, $R_{11}$, $R_{12}$, $R_{13}$, $R_{14}$ and $R_{15}$ are hydrogen.

19. The compound according to claim 17 wherein $R_{18}$ is hydrogen or halogen.

20. The compound according to claim 19 wherein $R_{18}$ is fluorine.

21. A compound of the formula:

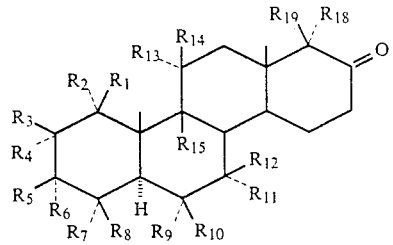

wherein
- $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;
- $R_5$ and $R_6$ are independently hydrogen, lower alkyl, halogen or lower alkoxy;
- $R_9$ and $R_{10}$ are independently hydrogen, lower alkyl, or halogen; and
- $R_{18}$ and $R_{19}$ are each independently hydrogen, lower alkyl containing from 2 to 6 carbon atoms, hydroxy, chloro or fluoro.

22. The compound according to claim 21 wherein the lower alkyl group of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ and lower alkoxy contain 1-3 carbon atoms.

23. The compound according to claim 21 wherein lower alkyl of $R_1$, $R_2$, $R_3$, $R_4$, $R_6$, $R_7$, $R_8$, $R_9$, $R_{10}$, $R_{11}$, $R_{12}$, $R_{13}$, $R_{14}$ and $R_{15}$ is methyl.

24. The compound according to claim 21 wherein said halogen is fluorine.

25. The compound according to claim 21 wherein $R_5$ is hydrogen or methyl.

26. The compound according to claim 23 wherein $R_1$, $R_2$, $R_3$, $R_4$, $R_6$, $R_7$, $R_8$, $R_9$, $R_{10}$, $R_{11}$, $R_{12}$, $R_{13}$, $R_{14}$ and $R_{15}$ are hydrogen.

27. The compound according to claim 23 wherein $R_{18}$ is hydrogen, fluorine or chlorine.

28. The compound according to claim 25 wherein $R_{18}$ is fluorine.

29. A compound of the formula:

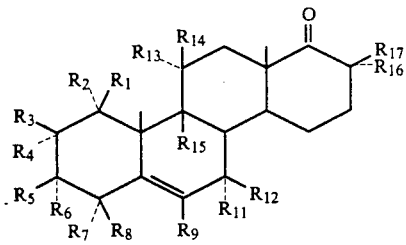

wherein $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;

$R_5$ and $R_6$ are independently hydrogen, lower alkyl, halogen or lower alkoxy;

$R_9$ is hydrogen, lower alkyl, or halogen; and $R_{16}$ and $R_{17}$ are each independently hydrogen, lower alkyl, hydroxy or halogen.

30. The compound according to claim 29 wherein the lower alkyl group and lower alkoxy group contain 1-3 carbon atoms.

31. The compound according to claim 29 wherein lower alkyl is methyl.

32. The compound according to claim 29 wherein halogen is fluorine.

33. The compound according to claim 29 wherein $R_5$ is hydrogen or methyl.

34. The compound according to claim 29 wherein $R_1$, $R_2$, $R_3$, $R_4$, $R_6$, $R_7$, $R_8$, $R_{10}$, $R_{11}$, $R_{12}$, $R_{13}$, $R_{14}$, and $R_{15}$ are hydrogen.

35. The compound according to claim 33 wherein $R_{16}$ is hydrogen or halogen.

36. The compound according to claim 35 wherein $R_{16}$ is fluorine.

37. A compound of the formula:

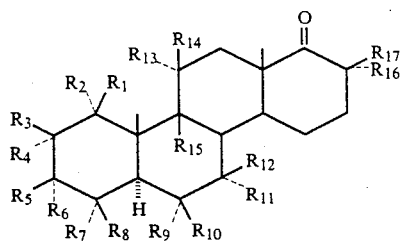

wherein $R_1$, $R_2$, $R_3$, $R_4$, $R_7$, $R_8$, $R_{11}$, $R_{12}$, $R_{13}$, $R_{14}$ and $R_{15}$ are each independently hydrogen, lower alkyl, halogen, hydroxy or lower alkoxy;

$R_5$ and $R_6$ are independently hydrogen, lower alkyl, halogen or lower alkoxy;

$R_9$ and $R_{10}$ are independently hydrogen, lower alkyl, or halogen; and $R_{16}$ and $R_{17}$ are each independently hydrogen, lower alkyl, containing from 2-6 carbon atoms, hydroxy, chlorine or fluorine, provided that when $R_1$–$R_{15}$ are all hydrogen, then at least one of $R_{16}$ and $R_{17}$ is hydroxy, fluoro, or chloro.

38. The compound according to claim 37 wherein the lower alkyl group of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ and lower alkoxy group contain 1-3 carbon atoms.

39. The compound according to claim 37 wherein the lower alkyl of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ is methyl.

40. The compound according to claim 37 wherein said halogen is fluorine.

41. The compound according to claim 37 wherein $R_5$ is hydrogen or methyl.

42. The compound according to claim 37 wherein $R_1$, $R_2$, $R_3$, $R_4$, $R_6$, $R_7$, $R_8$, $R_9$, $R_{10}$, $R_{11}$, $R_{12}$, $R_{13}$, $R_{14}$ and $R_{15}$ are hydrogen.

43. The compound according to claim 41 wherein $R_{16}$ is hydrogen, fluorine or chlorine.

44. The compound according to claim 43 wherein $R_{16}$ is fluorine.

45. A compound of the formula:

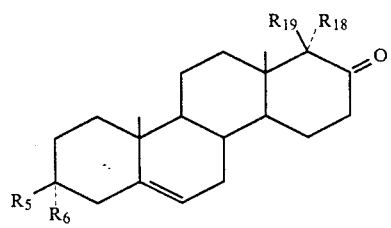

wherein $R_5$ and $R_6$ are independently lower alkyl or hydrogen;

$R_{18}$ and $R_{19}$ are independently hydrogen, lower alkyl or halogen.

46. The compound according to claim 45 wherein $R_5$ is lower alkyl or hydrogen and $R_6$ is hydrogen.

47. The compound according to claim 46 wherein the lower alkyl group contains 1-3 carbon atoms.

48. The compound according to claim 46 wherein lower alkyl is methyl.

49. The compound according to claim 45 wherein said halogen is fluorine.

50. The compound according to claim 46 wherein $R_{18}$ is fluorine, methyl or hydrogen and $R_{19}$ is hydrogen.

51. A compound of the formula:

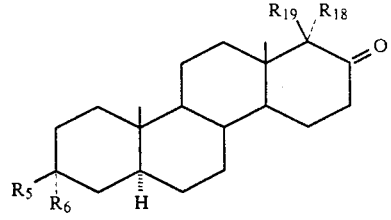

wherein $R_5$ and $R_6$ are independently lower alkyl or hydrogen;

$R_{18}$ and $R_{19}$ are independently hydrogen, lower alkyl containing 2-6 carbon atoms, fluorine or chlorine.

52. The compound according to claim 51 wherein $R_5$ is lower alkyl or hydrogen and $R_6$ is hydrogen.

53. The compound according to claim 52 wherein $R_5$ is alkyl containing 1-3 carbon atoms.

54. The compound according to claim 52 wherein $R_5$ is methyl.

55. The compound according to claim 51 wherein $R_{18}$ or $R_{19}$ is fluorine.

56. The compound according to claim 52 wherein $R_{18}$ is fluorine, or hydrogen and $R_{19}$ is hydrogen.

57. A compound of the formula:

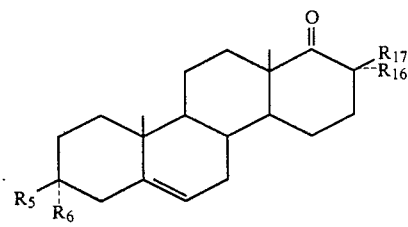

wherein

R₅ and R₆ are independently lower alkyl or hydrogen;

R₁₆ and R₁₇ are independently hydrogen, lower alkyl or halogen.

58. The compound according to claim 57 wherein R₅ is lower alkyl or hydrogen and R₆ is hydrogen.

59. The compound according to claim 58 wherein the lower alkyl group contains 1-3 carbon atoms.

60. The compound according to claim 58 wherein lower alkyl is methyl.

61. The compound according to claim 57 wherein said halogen is fluorine.

62. The compound according to claim 58 wherein R₁₆ is fluorine, methyl or hydrogen and R₁₇ is methyl.

63. A compound of the formula:

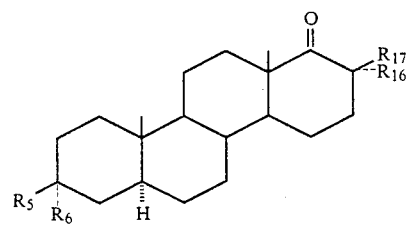

wherein

R₅ and R₆ are independently lower alkyl or hydrogen; and

R₁₆ and R₁₇ are independently hydrogen, lower alkyl containing from 2-6 carbon atoms, fluorine, chlorine or hydroxy, provided that when R₅ and R₆ are hydrogen, then at least one of R₁₆ and R₁₇ is fluoro, chloro, or hydroxy.

64. The compound according to claim 63 wherein R₅ is lower alkyl or hydrogen and R₆ is hydrogen.

65. The compound according to claim 64, wherein R₅ is alkyl containing 1-3 carbon atoms.

66. The compound according to claim 64 wherein R₅ is methyl.

67. The compound according to claim 64 wherein one of R₁₆ and R₁₇ is fluorine.

68. The compound according to claim 64 wherein R₁₆ is fluorine, or hydrogen and R₁₇ is methyl.

69. The compound according to claim 1 which is:

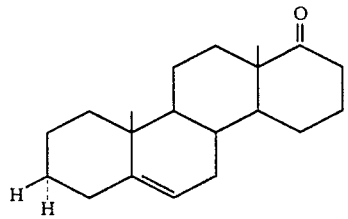

70. The compound according to claim 1 which is:

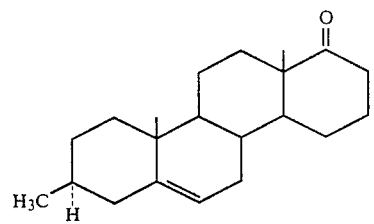

71. The compound according to claim 1 which is:

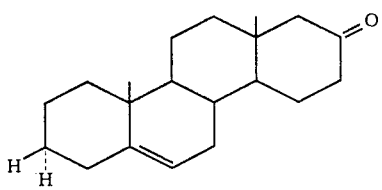

72. The compound according to claim 1 which is:

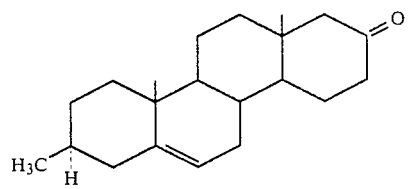

73. The compound according to claim 1 which is:

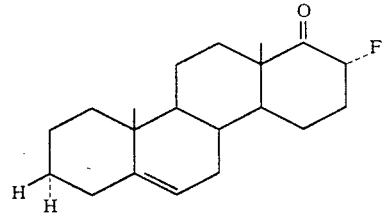

74. The compound according to claim 1 which is:

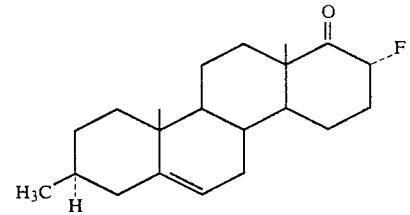

75. The compound according to claim 1 which is:

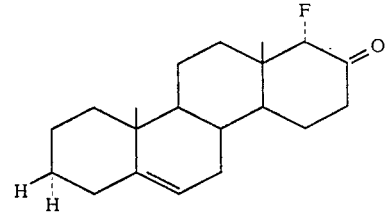

76. The compound according to claim 1 which is:

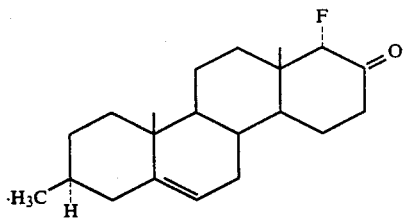

77. The compound according to claim 7 which is:

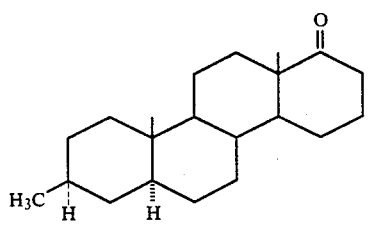

78. The compound according to claim 7 which is:

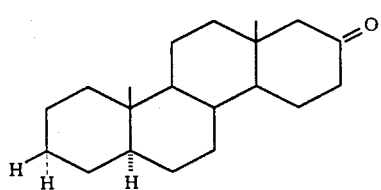

79. The compound according to claim 7 which is:

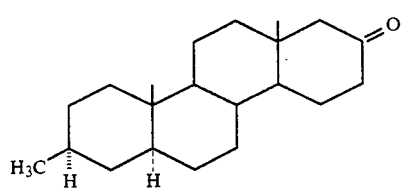

80. The compound according to claim 7 which is:

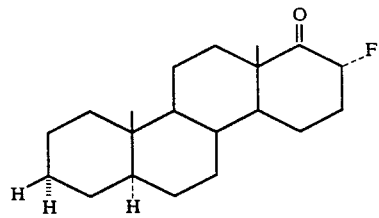

81. The compound according to claim 7 which is:

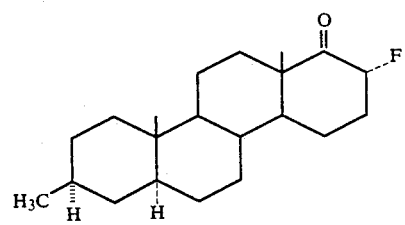

82. The compound according to claim 7 which is:

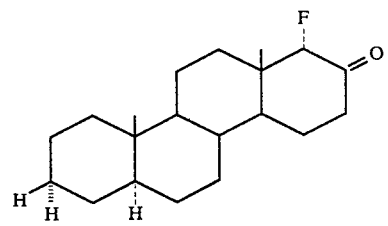

83. The compound according to claim 7 which is:

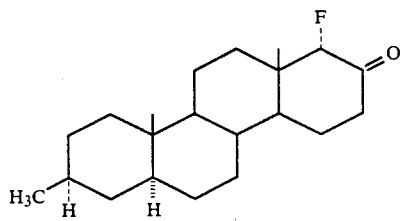

84. The compound according to claim 1 which is

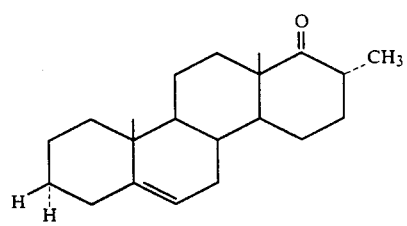

85. The compound according to claim 1 which is

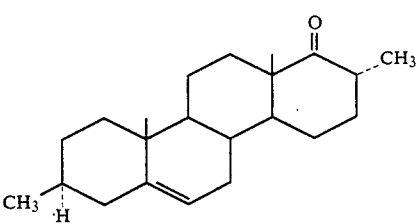

86. The compound according to claim 1 which is

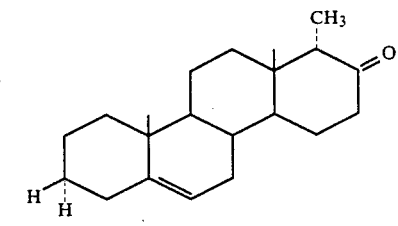

87. The compound according to claim 1 which is

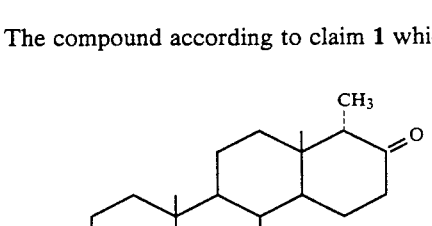
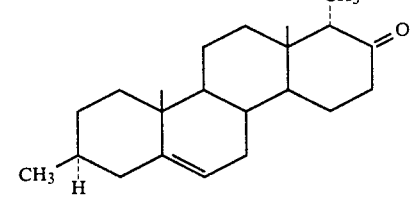

88. The compound according to claim 7 which is

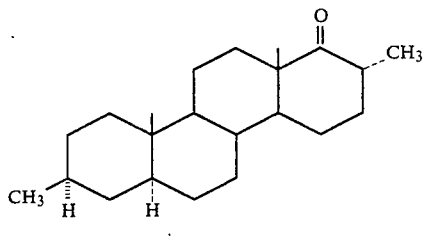

89. The compound according to claim 7 which is

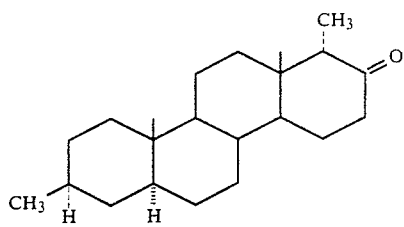

90. A pharmaceutical composition comprising a therapeutically effective amount of a compound according to claim 1 and a pharmaceutically acceptable carrier therefor.

91. A pharmaceutical composition comprising a therapeutically effective amount of a compound according to claim 7 and a pharmaceutically acceptable carrier therefor.

* * * * *

UNITED STATES PATENT AND TRADEMARK OFFICE
CERTIFICATE OF CORRECTION

Page 1 of 4

PATENT NO. : 5,028,631
DATED : July 2, 1991
INVENTOR(S) : Arthur G. Schwartz, et al.

It is certified that error appears in the above-indentified patent and that said Letters Patent is hereby corrected as shown below:

Column 3, line 11: "5$\beta$" should read as --5$\alpha$--

Column 3, line 12: "15$\beta$" should read as --15$\alpha$--

Column 3, line 32: "16$\beta$" should read as --16$\alpha$--

Column 3, line 49: delete second occurrence of "androsten-17-one"

Column 7, line 33: after "$R_{18}$" insert --or $R_{19}$--

Column 21, line 16: "hereabove" should read as --hereinabove--

Column 27, line 41: "6" should read as --6.--

Column 27, line 59: "3ones" should read as --3-ones--

Column 31, line 37: "5en-17-one" should read as --5-en-17-one--

Column 33, line 13: "9!" should read as --91--

Column 33, line 23: "(130" should read as --(13)--

UNITED STATES PATENT AND TRADEMARK OFFICE
CERTIFICATE OF CORRECTION

Page 2 of 4

PATENT NO. : 5,028,631
DATED : July 2, 1991
INVENTOR(S) : Arthur G. Schwartz, et al.

It is certified that error appears in the above-indentified patent and that said Letters Patent is hereby corrected as shown below:

Column 38, line 68: "DHFA" should read as --DHEA--

Column 40, line 55: "17ketal" should read as --17-ketal--

Column 42, lines 3 & 54: "17one" should read as --17-one--

Column 44, lines 1 & 48: "17one" should read as --17-one--

Column 45, line 47: "3one" should read as --3-one--

Column 47, line 40: "ene-18one" should read as --en-18-one--

Column 50, line 34: "yields." should read as --yields--

Column 50, line 65: "3-H." should read as --3-H--

Column 51, line 38: "16-a" should read as --17a--

Column 52, line 52: delete first occurrence of --11α "

UNITED STATES PATENT AND TRADEMARK OFFICE
CERTIFICATE OF CORRECTION

PATENT NO. : 5,028,631
DATED : July 2, 1991
INVENTOR(S) : Arthur G. Schwartz, et al.

It is certified that error appears in the above-indentified patent and that said Letters Patent is hereby corrected as shown below:

Column 53, line 36: before "iodine" insert --with--

Column 53, line 62: "? 7" should read as --17--

Column 54, line 16: "5enes" should read as --5-enes--

Column 54, line 19: "one-1" should read as --one 1--

Column 55, line 15: "wilson" should read as --Wilson--

Column 59, line 67: "17one" should read as --17-one--

Column 60, line 56: "17aβ" should read as --17aα--

Column 66, line 48: "dehydrogehae" should read as --dehydrogenase--

Column 63, line 10: "actIon" should read as --action--

UNITED STATES PATENT AND TRADEMARK OFFICE
CERTIFICATE OF CORRECTION

PATENT NO. : 5,028,631
DATED : July 2, 1991
INVENTOR(S) : Arthur G. Schwartz, et. al.

It is certified that error appears in the above-indentified patent and that said Letters Patent is hereby corrected as shown below:

Column 67, line 40, "$R_1 614 R_{15}$" should read as --$R_1-R_{15}$--.

Signed and Sealed this

Fifth Day of April, 1994

Attest:

BRUCE LEHMAN

*Attesting Officer*  *Commissioner of Patents and Trademarks*